United States Patent
Lee

(10) Patent No.: US 10,507,253 B2
(45) Date of Patent: Dec. 17, 2019

(54) NANOPARTICLE PROBES AND METHODS OF MAKING AND USE THEREOF

(71) Applicant: Paul C. Lee, Columbia, MD (US)

(72) Inventor: Paul C. Lee, Columbia, MD (US)

(*) Notice: Subject to any disclaimer, the term of this patent is extended or adjusted under 35 U.S.C. 154(b) by 38 days.

(21) Appl. No.: 15/680,016

(22) Filed: Aug. 17, 2017

(65) Prior Publication Data

US 2018/0000972 A1  Jan. 4, 2018

Related U.S. Application Data

(63) Continuation-in-part of application No. 15/461,035, filed on Mar. 16, 2017.

(60) Provisional application No. 62/309,751, filed on Mar. 17, 2016.

(51) Int. Cl.
| | | |
|---|---|---|
| A61K 49/00 | (2006.01) | |
| G01N 33/58 | (2006.01) | |
| G01N 33/68 | (2006.01) | |
| G01N 33/543 | (2006.01) | |

(52) U.S. Cl.
CPC ... *A61K 49/0093* (2013.01); *G01N 33/54346* (2013.01); *G01N 33/587* (2013.01); *G01N 33/6842* (2013.01); *G01N 33/6893* (2013.01); *G01N 2400/40* (2013.01); *G01N 2800/042* (2013.01); *G01N 2800/321* (2013.01); *G01N 2800/347* (2013.01)

(58) Field of Classification Search
CPC .......... G01N 33/587; G01N 33/54346; G01N 2400/00; G01N 33/6842; G01N 33/5308; A61K 49/0093
See application file for complete search history.

(56) References Cited

U.S. PATENT DOCUMENTS

| | | |
|---|---|---|
| 9,044,385 B2 | 6/2015 | Pacetti et al. |
| 9,072,665 B2 | 7/2015 | Ludwig et al. |
| 2004/0067544 A1 | 4/2004 | Vogel et al. |
| 2005/0180945 A1 | 8/2005 | Chaikof et al. |
| 2006/0251580 A1 | 11/2006 | Keppler et al. |
| 2009/0325259 A1 | 12/2009 | Vogel et al. |
| 2010/0028902 A1 | 2/2010 | Brown et al. |
| 2010/0104506 A1 | 4/2010 | Ludwig et al. |
| 2010/0304424 A1 | 12/2010 | Vink et al. |
| 2015/0023875 A1 | 1/2015 | Farokhzad et al. |
| 2015/0140598 A1 | 5/2015 | Daniels et al. |
| 2015/0160214 A1 | 6/2015 | Auton |
| 2017/0269095 A1 | 3/2017 | Lee |

OTHER PUBLICATIONS

Becker BF, Chappell D, Bruegger D, Annecke T, Jacob M. Therapeutic strategies targeting the endothelial glycocalyx: acute deficits, but great potential. Cardiovasc Res. 2010;87(2):300-10. doi: 10.1093/cvr/cvq137. PubMed PMID: 20462866.

Calderon AJ, Baig M, Pichette B, Muzykantov V, Muro S, Eckmann DM. Effect of Glycocalyx on Drug Delivery Carriers Targeted to Endothelial Cells. Int J Transp Phenom. 2011;12(1-2):63-75. PubMed PMID: 22679359; PMCID: PMC3367256.

Farr, et al., "Imaging Early Endothelial Inflammation Following Stroke by Core Shell Silica Superparamagnetic Glyconanoparticles That Target Selectin," American Chemical Society Publications, Nano Letters, 2014, 14, pp. 2130-2134.

Graf F LC, Janssen B, Ingber DE, Shih WM. Controlling cellular uptake of nanoparticles by designing their shape using DNA origami. Doctoral Dissertation, Harvard University. 2012.

Hartman, et al., "Supported lipid bilayers as dynamic platforms for tethered particles," Royal Society of Chemistry, Nanoscale, 2015, vol. 7, pp. 66-76.

Kannan RM, Nance E, Kannan S, Tomalia DA. Emerging concepts in dendrimer-based nanomedicine: from design principles to clinical applications. J Intern Med. 2014;276(6):579-617. doi: 10.1111/joim.12280. PubMed PMID: 24995512.

Liu, et al., "Multivalent Binding of Nanocarrier to Endothelial Cells under Shear Flow," Biophysical Journal, Jul. 2011, vol. 101, pp. 319-326.

Marchi AN, Saaem I, Vogen BN, Brown S, LaBean TH. Toward larger DNA origami. Nano Lett. 2014;14(10):5740-7. doi: 10.1021/nl5026265. PubMed PMID: 25179827.

Onyskiw et al., "Effect of PEGylation on Ligand-Based Targeting of Drug Carriers to the Vascular Wall in Blood Flow," American Chemical Society Publications, Langmuir, 2013, 29, pp. 11127-11134.

Palcic MM, Li H, Zanini D, Bhella RS, Roy R. Chemoenzymatic synthesis of dendritic sialyl Lewis(x). Carbohydr Res. 1997;305(3-4):433-42. PubMed PMID: 9648262.

Rajendran A, Endo M, Sugiyama H. DNA origami: synthesis and self-assembly. Curr Protoc Nucleic Acid Chem. 2012;Chapter 12:Unit 12 9 1-8. doi: 10.1002/0471142700.nc1209s48. PubMed PMID: 22395964.

Shaw A, Benson E, Hogberg B. Purification of functionalized DNA origami nanostructures. ACS Nano. 2015;9(5):4968-75. doi: 10.1021/nn507035g. PubMed PMID: 25965916.

Slooter MD, Bierau K, Chan AB, Lowik CW. Near infrared fluorescence imaging for early detection, monitoring and improved intervention of diseases involving the joint. Connect Tissue Res. 2015;56(2):153-60. doi: 10.3109/03008207.2015.1012586. PubMed PMID: 25689091.

Türkcan, et al., "Receptor Displacement in the Cell Membrane by Hydrodynamic Force Amplification through Nanoparticles," Biophysical Journal, Jul. 2013, vol. 105, pp. 116-126.

Van Kasteren et al., "Glyconanoparticles allow pre-symptomatic in vivo imaging of brain disease," PNAS, Jan. 2009, vol. 106, No. 1, pp. 18-23.

Andersen E, Nielsen M., "DNA origami design of 3D nanostructures." Protocol Exchange. 2009. doi: 10.1038/nprot.2009.75.

*Primary Examiner* — Robert S Cabral

(74) *Attorney, Agent, or Firm* — Knobbe, Martens, Olson & Bear LLP

(57) ABSTRACT

Some embodiments relate to nanoparticle probes for the detection of disease states in a patient or for tissue engineering. In some embodiments, the nanoparticle probe comprises one or more slip bonds that bind to a cell surface structure. In some embodiments, the binding of the nanoparticle probe is selective. In some embodiments, the nanoparticle probe binds to cells having a certain maximum glycocalyx thickness.

16 Claims, 14 Drawing Sheets

Specification includes a Sequence Listing.

SEQUENCE LISTING

<160> NUMBER OF SEQ ID NOS: 1

<210> SEQ ID NO 1
<211> LENGTH: 7249
<212> TYPE: DNA
<213> ORGANISM: Artificial Sequence
<220> FEATURE:
<223> OTHER INFORMATION: origami construct

<400> SEQUENCE: 1

| | | | | | |
|---|---|---|---|---|---|
| aatgctacta | ctattagtag | aattgatgcc | accttttcag | ctcgcgcccc | aaatgaaaat 60 |
| atagctaaac | aggttattga | ccatttgcga | aatgtatcta | atggtcaaac | taaatctact 120 |
| cgttcgcaga | attgggaatc | aactgttaca | tggaatgaaa | cttccagaca | ccgtacttta 180 |
| gttgcatatt | taaaacatgt | tgagctacag | caccagatta | agcaattaag | ctctaagcca 240 |
| tccgcaaaaa | tgacctctta | tcaaaaggag | caattaaagg | tactctctaa | tcctgacctg 300 |
| ttggagtttg | cttccggtct | ggttcgcttt | gaagctcgaa | ttaaaacgcg | atatttgaag 360 |
| tctttcgggc | ttcctcttaa | tcttttgat | gcaatccgct | ttgcttctga | ctataatagt 420 |
| cagggtaaag | acctgatttt | tgatttatgg | tcattctcgt | tttctgaact | gtttaaagca 480 |
| tttgaggggg | attcaatgaa | tatttatgac | gattccgcag | tattggacgc | tatccagtct 540 |
| aaacatttta | ctattacccc | ctctggcaaa | acttcttttg | caaagcctc | tcgctatttt 600 |
| ggtttttatc | gtcgtctggt | aaacgagggt | tatgatagtg | ttgctcttac | tatgcctcgt 660 |
| aattcctttt | ggcgttatgt | atctgcatta | gttgaatgtg | gtattcctaa | atctcaactg 720 |
| atgaatcttt | ctacctgtaa | taatgttgtt | ccgttagttc | gttttattaa | cgtagatttt 780 |
| tcttcccaac | gtcctgactg | gtataatgag | ccagttctta | aaatcgcata | aggtaattca 840 |
| caatgattaa | agttgaaatt | aaaccatctc | aagcccaatt | tactactcgt | tctggtgttc 900 |
| tcgtcagggc | aagccttatt | cactgaatga | gcagctttgt | tacgttgatt | tgggtaatga 960 |
| atatccggtt | cttgtcaaga | ttactcttga | tgaaggtcag | ccagcctatg | cgcctggtct 1020 |
| gtacaccgtt | catctgtcct | cttcaaagt | tggtcagttc | ggttccctta | tgattgaccg 1080 |
| tctgcgcctc | gttccggcta | agtaacatgg | agcaggtcgc | ggatttcgac | acaatttatc 1140 |
| aggcgatgat | acaaatctcc | gttgtacttt | gtttcgcgct | tggtataatc | gctggggtc 1200 |
| aaagatgagt | gttttagtgt | attctttcgc | ctctttcgtt | ttaggttggt | gccttcgtag 1260 |
| tggcattacg | tatttaccc | gtttaatgga | aacttcctca | tgaaaaagtc | tttagtcctc 1320 |
| aaagcctctg | tagccgttgc | taccctcgtt | ccgatgctgt | ctttcgctgc | tgagggtgac 1380 |
| gatcccgcaa | aagcggcctt | taactccctg | caagcctcag | cgaccgaata | tatcggttat 1440 |
| gcgtgggcga | tggttgttgt | cattgtcggc | gcaactatcg | gtatcaagct | gtttaagaaa 1500 |
| ttcacctcga | aagcaagctg | ataaaccgat | acaattaaag | ctccttttg | agccttttt 1560 |
| ttttggagat | tttcaacgtg | aaaaaattat | tattcgcaat | tcctttagtt | gttcctttct 1620 |
| attctcactc | cgctgaaact | gttgaaagtt | gtttagcaaa | accccataca | gaaaattcat 1680 |
| ttactaacgt | ctggaaagac | gacaaaactt | tagatcgtta | cgctaactat | gagggttgtc 1740 |
| tgtggaatgc | tacaggcgtt | gtagtttgta | ctggtgacga | aactcagtgt | tacggtacat 1800 |
| gggttcctat | tgggcttgct | atccctgaaa | atgagggtgg | tggctctgag | ggtggcggtt 1860 |
| ctgagggtgg | cggttctgag | ggtggcggta | ctaaacctcc | tgagtacggt | gatacaccta 1920 |
| ttccgggcta | tacttatatc | aaccctctcg | acggcactta | tccgcctggt | actgagcaaa 1980 |
| accccgctaa | tcctaatcct | tctcttgagg | agtctcagcc | tcttaatact | ttcatgtttc 2040 |

-continued

```
agaataatag gttccgaaat aggcaggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgaag    2220
atccattcgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgaggag gcggttccgg tggtggctct ggttccggtg    2400
attttgatta tgaaaagatg gcaaacgcta ataagggggc tatgaccgaa aatgccgatg    2460
aaaacgcgct acagtctgac gctaaaggca aacttgattc tgtcgctact gattacggtg    2520
ctgctatcga tggttttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttag cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttactttttct    2940 taaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcatttttga cgttaaacaa aaaatcgttt cttatttgga    3180
ttgggataaa taatatggct gtttatttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt acttacctt     3660 ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840 ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta taaacccaa cctaagccgg    4020 aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta atgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
```

```
gttttacgtg ctaataattt tgatatggtt ggttcaattc cttccataat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgcaccta agatatttt agataaccttt cctcaattcc tttctactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt cccttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa aagtattgc tacaacggtt aatttgcgtg atggacagac tcttttactc    5340
ggtggcctca ctgattataa aaacacttct caagattctg gcgtaccgtt cctgtctaaa    5400 atcccttta tcggcctcct gtttagctcc cgctctgatt ccaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760 gttgagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcgctgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg aattcgagct    6240
cggtacccgg ggatcctcta gagtcgacct gcaggcatgc aagcttggca ctggccgtcg    6300
ttttacaacg tcgtgactgg gaaaaccctg gcgttaccca acttaatcgc cttgcagcac    6360 atccccctt cgccagctgg cgtaatagcg aagaggcccg caccgatcgc ccttcccaac    6420
agttgcgcag cctgaatggc gaatggcgct ttgcctggtt tccggcacca gaagcggtgc    6480
cggaaagctg gctggagtgc gatcttcctg aggccgatac ggtcgtcgtc ccctcaaact    6540
ggcagatgca cggttacgat gcgcccatct acaccaacgt aacctatccc attacggtca    6600
atccgccgtt tgttcccacg gagaatccga cgggttgtta ctcgctcaca tttaatgttg    6660
atgaaagctg gctacaggaa ggccagacgc gaattatttt tgatggcgtt cctattggtt    6720
aaaaaatgag ctgatttaac aaaaatttaa cgcgaatttt aacaaaatat taacgtttac    6780
aatttaaata tttgcttata caatcttcct gtttttgggg cttttctgat tatcaaccgg    6840
```

```
ggtacatatg attgacatgc tagttttacg attaccgttc atcgattctc ttgtttgctc      6900
cagactctca ggcaatgacc tgatagcctt tgtagatctc tcaaaaatag ctaccctctc      6960
cggcattaat ttatcagcta gaacggttga atatcatatt gatggtgatt tgactgtctc      7020
cggcctttct caccctttg aatctttacc tacacattac tcaggcattg catttaaaat       7080
atatgagggt tctaaaaatt tttatccttg cgttgaaata aaggcttctc ccgcaaaagt      7140
attacagggt cataatgttt ttggtacaac cgatttagct ttatgctctg aggctttatt      7200
gcttaatttt gctaattctt tgccttgcct gtatgattta ttggatgtt                  7249
```

NANOPARTICLE PROBES AND METHODS OF MAKING AND USE THEREOF

CROSS REFERENCE TO RELATED APPLICATIONS

The present application is a continuation-in-part of U.S. patent application Ser. No. 15/461,035, Filed Mar. 16, 2017, which claims the priority benefit of U.S. Patent Application No. 62/309,751, filed Mar. 17, 2016, all of which are hereby incorporated by reference in their entireties.

REFERENCE TO SEQUENCE LISTING

A Sequence Listing submitted as an ASCII text file via EFS-Web is hereby incorporated by reference in accordance with 35 U.S.C. 1.52(e). The name of the ASCII text file for the Sequence Listing is PLEE001P1.TXT, the date of creation of the ASCII text file is Oct. 22, 2019, and the size of the ASCII text file is 9.6 KB.

BACKGROUND

Field

The present disclosure pertains to nanoparticle probes, methods of making nanoparticle probes, and methods of using nanoparticle probes for biological targeting.

Description of the Related Art

The glycocalyx layer covers the surfaces of various cell types and is comprised of glycoproteins and other carbohydrate-based moieties.

SUMMARY

Some embodiments described herein pertain to nanoparticle probes. In some embodiments, the nanoparticle probes can be used for cell targeting. In some embodiments, cells are targeted based on the thickness of their glycocalyx.

In some embodiments, the nanoparticle probe comprises one or more of a nanoparticle base structure and a slip bond moiety. In some embodiments, the nanoparticle probe comprises one or more of a nanoparticle base structure and a high affinity moiety. In some embodiments, the slip bond moiety is configured to form reversible bonds to a target structure of a cell. In some embodiments, the slip bond moiety's target structure is or is on the surface of a glycocalyx of the cell (e.g., a surface protein; glycoprotein, saccharide, etc.). In some embodiments, the high affinity moiety preferentially binds to a target structure of the cell at the cell surface. In some embodiments, the nanoparticle probe binds to the target cell at least in part based on its accessibility to the cell surface or the thickness of a glycocalyx layer of the cell.

Any of the embodiments described above, or described elsewhere herein, can include one or more of the following features.

In some embodiments, the nanoparticle probe further comprises a tether functionalized to the nanoparticle base structure and to the slip bond and/or the high affinity moiety (e.g., an associative moiety). In some embodiments, the high affinity moiety binds strongly and/or irreversibly to a cell surface protein, etc. In some embodiments, the tether forms a connection from the nanoparticle base structure to the slip bond and/or high affinity moiety.

In some embodiments, the slip bond has a binding strength of less than about 100 pN.

In some embodiments, the high affinity moiety has a binding strength of larger than 100 pN.

Some embodiments pertain to methods of diagnosing disease states. Some embodiments pertain to methods of diagnosing dysfunctional tissue. In some embodiments, the method of diagnosing dysfunctional tissue in a patient comprises administering the nanoparticle probes described above to the patient. In some embodiments, the method of diagnosing dysfunctional tissue comprises detecting a nanoparticle probe in a patient.

BRIEF DESCRIPTION OF THE DRAWINGS

The features of the nanoparticle probes disclosed herein are described below with reference to the drawings of certain embodiments. The illustrated embodiments are intended to demonstrate, but not to limit, the present disclosure. The proportions and relative dimensions and sizes of each component as shown in these drawings forms part of the supporting disclosure of this specification, but should not be limiting on the scope of this specification, except to the extent that such proportions, dimensions, or sizes are included in any individual claims. The drawings contain the following Figures:

FIG. 12A shows the starting targeting nanoparticle. FIG. 12B shows the degradation of a coating over the core of the nanoparticle after time has passed.

DETAILED DESCRIPTION

Figure 1B:
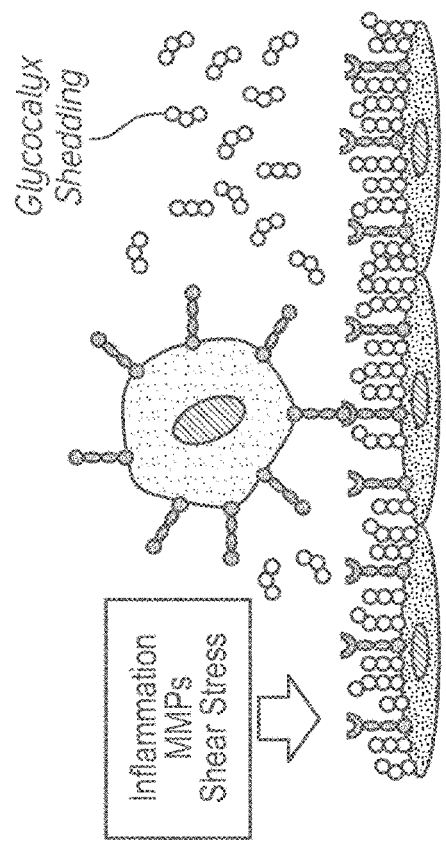
FIG. 1A-B show a schematic of a circulating tumor cell.

Some embodiments of the present disclosure pertain to nanoparticle probes, methods of making the same, and methods of using the same for biological targeting and analyses. Some embodiments disclosed herein pertain to nanoparticle probes (and methods for manufacturing and using the same) having features that allow them to differentiate between cells. In some embodiments, the nanoparticle probes described herein can differentiate groups of cells by variations in the glycocalyx layers of those cells. While several embodiments are discussed below in reference to "nanoparticles" or "nanoparticle probes," it should also be understood that, while the prefix "nano" is used (e.g., having a dimension and/or diameter of equal or less than about 1 nm to about 1000 nm), this prefix is illustrative. It should be understood that the features and improvements described herein are also applicable to microprobes and microparticles (e.g., having a dimension and/or diameter greater than or equal to about 1 μm to about 100 μm). Any features, structure, or step disclosed herein can be omitted. While the illustrated examples include features, these features need not be present in all embodiments. Further, for purposes of summarizing the disclosure, certain aspects, advantages, and features of the inventions have been described herein. However, not all embodiments include or achieve any or all of those aspects, advantages, and features.

Non-communicable diseases, such as Type 2 diabetes, hypertension, and chronic kidney disease, are a leading cause of death and disability worldwide. Without a definite cure and due to the multi-causal nature of the diseases, modern medicine is limited in treating these disease states. For example, unless early prevention is possible, medicine is capable of only treatment of symptoms. In rare cases though, remission without relapse can occur in response to exercise, diet, and mechanical stimulation-based therapies. This result suggests that the biological mechanisms of disease treatment can offer successful health outcomes for patients. If the mechanisms behind self-repair can be probed and understood, these biological responses can be bolstered, facilitated, and/or stimulated, treating of the underlying cause of the disease. For that reason, elucidation of the biological mechanisms of disease may lead to novel therapies. In some embodiments, the nanoparticle probes disclosed herein allow early diagnosis of the above disease states and/or diagnosis before acute symptoms occur.

It has been noted that there is currently a lack of technology that effectively investigates the biological phenomena and biological processes (e.g., outcomes) underlying these disease states. Some embodiments described herein provide diagnostic methods and devices for probing biological systems. In some embodiments, the techniques and devices disclosed herein can probe biological systems to better understand the disease, disease progression, and/or disease treatment. In some embodiments, the techniques and devices can be used to effectively treat the disease. In some embodiments, nanoparticle probes are used to accomplish these outcomes (e.g., to investigate biological systems, etc.). In some embodiments, by probing biological systems using nanoparticle probes, treatment and/or elucidation of diseases (e.g., by understanding the mechanisms underlying a disease state or disorder) can be accomplished. In some embodiments, biological mechanisms of disease states and disorders can be elucidated and the development of novel treatment methods for disease can be developed. Some embodiments pertain to facilitating biological responses and/or treating of the underlying cause of the disease using nanoparticle probes.

Some embodiments described herein pertain to nanoparticle probes that differentiate between groups of cells. In some embodiments, healthy cells can be targeted using the nanoparticle probes disclosed herein. In some embodiments, non-healthy cells can be targeted using the nanoparticle probes disclosed herein. In some embodiments, cell targeting is achieved by interactions between the nanoparticle probes disclosed herein and moieties at the cell surface (or in the cell). In some embodiments, the nanoparticle probes bind reversibly and/or irreversibly to target cells. In some embodiments, the cell surface-binding is based on associations between the nanoparticle probes and cell moieties (e.g., motifs, cell surface ligands, cell surface markers, cell surface receptors, surface proteins etc.).

In some embodiments, nanoparticle probes target cells based on one or more properties of the cell's glycocalyx. The glycocalyx is a layer that covers the surfaces of various cell types. It is comprised of glycoproteins and other carbohydrate-based moieties. The glycocalyx composition and structure varies depending on the cell and, in some cases, whether the cell is in a state of disease or not. For instance, the thickness of certain glycocalyx layers can range from less than 100 nm to several micrometers, depending on the cell type and/or the surrounding conditions (e.g. salt excess result in coalescing of certain glycans, leading to EC glycocalyx shrinkage and stiffening, which is potentially associated with endothelial dysfunction). In some embodiments, variations in cell glycocalyx layers can be exploited for nanoparticle probe targeting by using tailored binding motifs of the nanoparticle probe.

In some embodiments, the nanoparticles disclosed herein can be functionalized (e.g., through covalent bonds, binding, etc.) with cell-targeting ligands. In some embodiments, the nanoparticle is functionalized with one or more of folate, sialyl Lewis X, biotin, streptavidin, RGD, DNA and/or RNA origami, and/or combinations thereof. In some embodiments, the nanoparticle probes comprise ligands that bind to one or more cell surface targets including inflammatory markers (e.g. E-selectin), cell surface glycoproteins (e.g. ICAM-1), and/or mechanoreceptors (e.g. CD29).

The thickness of a cell's glycocalyx is an important biomarker of chronic inflammation. The glycocalyx layer covers the surfaces of various cell types and is comprised of glycoproteins and other carbohydrate-based moieties. The glycocalyx thickness can range from less than 100 nm to several micrometers (e.g., about 1 μm to about 10 μm or about 100 μm). The thickness of the glycocalyx depends on the cell type and surrounding environmental conditions. The overall structure acts as a mechanosensor that physically detects the surrounding fluid shear stress (FSS) through FSS-dependent integrins, syndecans, primary cilia, and other mechanoreceptors. Mechanical deformation results in downstream signaling and activation of shear responsive elements. In some embodiments, these mechanosensory properties can be exploited and targeted using the nanoparticle probes functionalized with selectable binding groups, as described elsewhere herein.

The glycocalyx of endothelial cells (EC) behaves in a somewhat unique fashion. For example, the EC glycocalyx is capable of adaptive remodeling over time. Additionally, in certain environments, the glycocalyx of EC cells thins compared to other cell types or compared to other EC cells in different environments. In inflammatory and/or hypoxic conditions, such as is found in diabetic patients, various factors (e.g., C-reactive protein, reactive oxygen species, advanced glycation end-products, etc.) can lead to the degradation or thinning of the EC glycocalyx. In some circumstances, this thinning is found in capillaries, though it may be noted in various blood vessel structures. ECs in low FSS regions, such as capillaries, express a thin glycocalyx, whereas ECs in high FSS regions, such as arteries, express a thicker glycocalyx. Mechanosensitivity can be dependent on multiple factors, including glycocalyx composition, thickness, and other variables, such as cross-linkages. Ignoring the biological and mechanical complexity of the glycocalyx and mechanoreceptors, some of which is still under investigation or unknown, the following general observations are made: (1) a thinner glycocalyx increases mechanosensor sensitivity; (2) when the glycocalyx thickness decreases to a point where the glycocalyx is no longer intact (e.g. deglycanated fibers do not induce sufficient hydrodynamic drag force to pull on FSS mechanoreceptors, such as apical B1 integrins), there will be reduced mechanosensitivity, (3) in very high FSS, found in certain pathophysiological conditions, glycocalyx shedding dominates, resulting in either a thinner glycocalyx or EC denudation from shear injury.

Figure 1A:
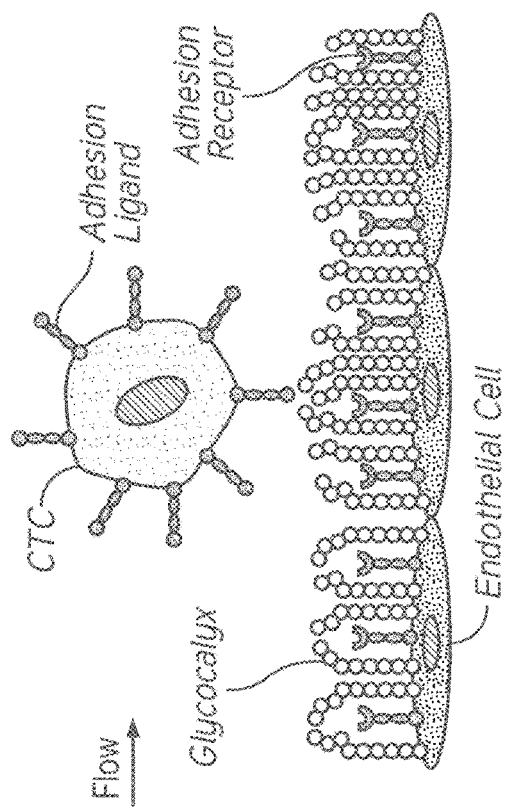

In some circumstances, the glycocalyx thickness is greater than the length of the tether and the nanoparticle probe does not bind to adhesion receptors on a cell surface. FIG. 1A demonstrates physiological conditions, where glycocalyx thickness exceeds the length of adhesion receptors and most surface receptors (not shown). In some circumstances, the glycocalyx thickness is less than the length of the tether and the nanoparticle probe does bind to adhesion receptors on a cell surface. FIG. 1B displays a pathophysiological state, where low FSS, inflammation, and hypoxic conditions result in glycocalyx shedding, thus increasing the chance for tumor cell binding during metastasis via exposure of integrin receptors (~11 nm height). The spacing between carbohydrate complexes or glycans are typically 20 nm apart. In some embodiments, the nanoparticle probes bind to these cells and can be used to identify and/or deliver therapeutics to these cells.

Figure 2:
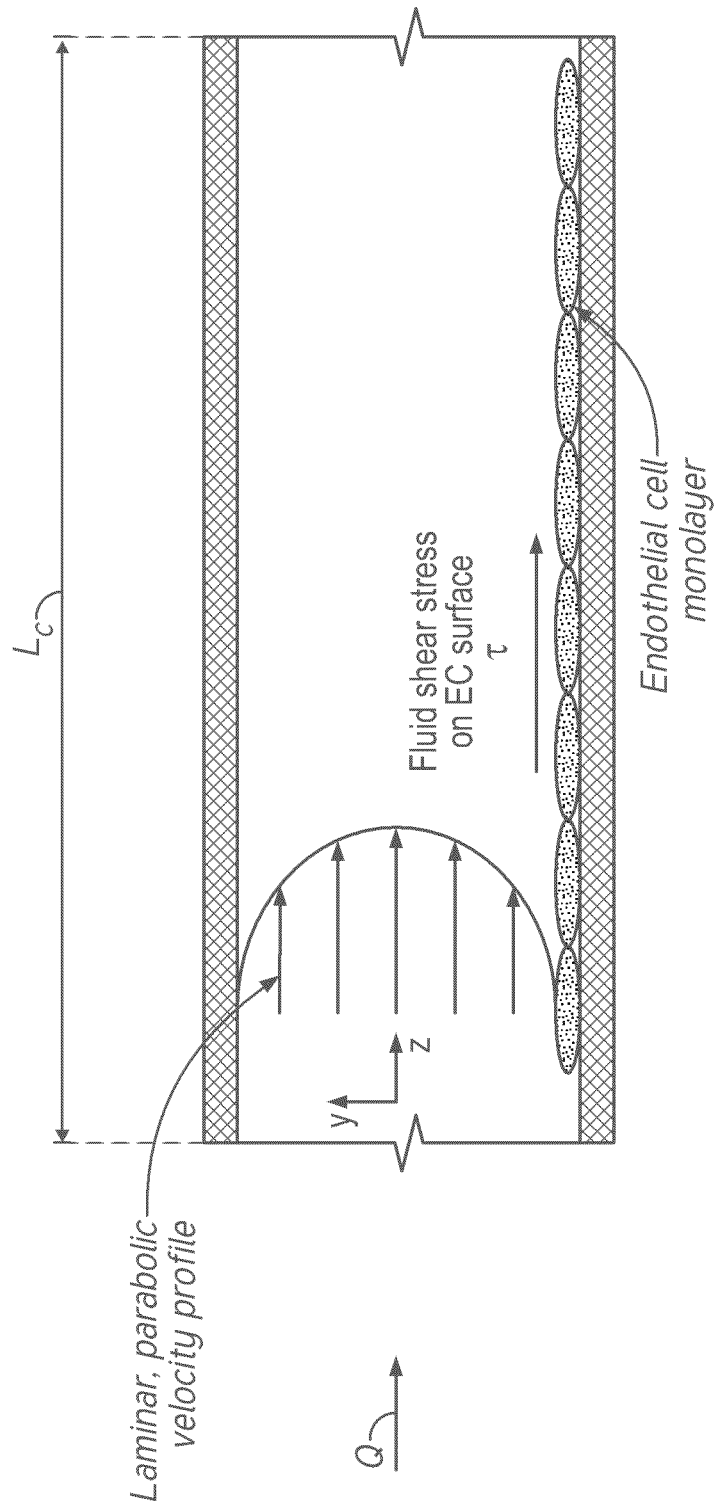
FIG. 2 shows a fluid shear stress model in endothelial cells lining blood vessels.

Additionally, there is an association between low basal chronic inflammation, low FSS, and glycocalyx degradation (i.e., thinning of the glycocalyx/thickness reduction) in ECs. Flow and mass transfer are important in biological systems. Systemic fluid flow not only encompasses the cardiovascular, lymphatic, and primo-vascular system, but also includes interstitial fluid and fascia for signaling and maintenance. When fluid flows along a material, there is a perpendicular force or FSS along the contacted boundary surface area, and shear rate is the velocity gradient dependent on the fluid viscosity and FSS. FSS in the microcirculation occurs on EC surfaces along the walls of capillaries and other vessels. Plasma viscosity affects mass transfer, and there is a strong correlation between increased viscosity or "stickiness" in biological fluids and various pathophysiological conditions. FIG. 2 shows a fluid shear stress model in endothelial cells lining blood vessels. Fluid shear stress is the force experienced perpendicular to the contacted EC surface area ($\tau=F/A$). Shear rate is expressed by the change in velocity between two flow layers ($\gamma=dz/dy$). The diameter of capillaries can be as small as 3 μm. Capillary density is about 600/mm$^3$, equivalent to about 40 μm between adjacent capillaries of about 1 mm length.

Cell properties, such as changes in glycocalyx thickness, can be pathophysiological indicators of disease (e.g., an early indicator prior to acute symptoms). In some embodiments, the nanoparticle probes disclosed herein target cells in environments demonstrating low basal chronic inflammation, low fluid shear stress (FSS), and cells with glycocalyx degradation. In some embodiments, the nanoparticle probes described herein associate with cells having thinning glycocalyx layers (e.g., by associating with one or more adhesion receptors of the cell) or with thinning glycocalyx layers themselves. In some embodiments, the presence of a disease state or a type of disease state itself can be determined by measuring the thickness of the glycocalyx. For example, in some embodiments the nanoparticle probes (e.g., functionalized nanoparticles, etc.) are able to target cells (e.g., diseased cells or cells indicating the presence of a disease state, etc.) based on the glycocalyx thickness. In some embodiments, the nanoparticle probes selectively bind to cells based on whether they have a glycocalyx above, equal to, or below a certain thickness. In some embodiments, the nanoparticles target cells having a glycocalyx below a targeted thickness threshold. In some embodiments, because the surrounding flow properties of fluid around a cell can determine the thickness of a cell's glycocalyx, the nanoparticle probes are able to indicate and/or target cells depending on the flow properties their environment. In some embodiments, the nanoparticle probes can target cells with glycocalyx thickness (e.g., measured from the cell surface to the terminus or average terminus of the glycocalyx) of less than or equal to about: 5 nm, 15 nm, 50 nm, 100 nm, or ranges including and/or spanning the aforementioned values. In some embodiments, the early pathophysiology of parenchyma can be detected with this method.

In some embodiments, the nanoparticle probes adhere to cells that reside in specific flow conditions (e.g., fluid shear stress conditions) and do not adhere to cells in other flow conditions. For instance, in some embodiments, the nanoparticle probes adhere to cells residing in an environment at a certain minimum fluid shear stress or flow rate. In some embodiments, the nanoparticle probes adhere to cells residing in an environment where the fluid shear stress is less than or equal to about: 0.01, 0.1, 1, 5, 10 dynes/cm$^2$, or ranges including and/or spanning the aforementioned values. In some embodiments, the nanoparticle probes adhere to cells residing in an environment where flow rate less than or equal to about is about 0.01, 0.02, 0.05, 0.10, 0.20, 0.50 mm/sec, or ranges including and/or spanning the aforementioned values. In some embodiments, detachment of the nanoparticle probe to the cell target in flow conditions is dependent on changes in on-off binding rate due to increasing hydrodynamic drag or increased holding/unbinding force. In some embodiments, detachment of the nanoparticle probe occurs at the blood-endothelial interface where fluid velocity is increased near capillary walls. In some embodiments, the nanoparticle probes adhere to cells residing in an environment at a certain maximum fluid shear stress. In some embodiments, nanoparticle probes adhere to cells residing in an environment where the maximum fluid shear stress is less than or equal to about 10, 15, 20 dynes/cm$^2$, or ranges including and/or spanning the aforementioned values. In some embodiments, the maximum flow rate is about 0.50, 1, 3, 5, 7 mm/sec, or ranges including and/or spanning the aforementioned values.

Nanoparticle probes can be trapped in collapsed capillaries (if capillaries were initially opened from increased blood circulation but is followed by pressure lower than the interstitial fluid). Minimum FSS ranges in capillaries may be present in local hypoxic regions, due to insufficient blood flow from increased fibrinogen content. In some embodiments, nanoparticle probes capable of accessing interstitial fluid flow can buildup in low FSS regions of the interstitial fluid. Minimum FSS ranges in larger vessels are found in aneurysms. Maximum FSS ranges in larger vessels result in endothelial denudation from shear injury.

While targeting and detecting cells with variable glycocalyx thicknesses to investigate and/or treat disease states is one potential use of the nanoparticle probes described herein, these nanoparticle probes can be used in a variety of applications. For instance, the technologies described herein find application in theranostic nanomedicine, regenerative medicine, tissue engineering, and basic research in mechanotransduction. In some embodiments, the proposed technology can have a large impact in both medicine (e.g., medical treatment of disease and diagnosis) and diagnostic research (e.g., research in in vitro and in vivo applications).

The nanoparticle probes can have a variety of configurations that allow it to bind to target cells. In some embodiments, the nanoparticle probe comprises one or more of a nanoparticle base structure (e.g., a nanoparticle, a core, etc.), a tether (e.g., an extension that can protrude from the nanoparticle), a hinge, and/or an associative moiety. In some embodiments, the nanoparticle probe lacks one or more of a nanoparticle base structure (e.g., a nanoparticle, a core, etc.), a tether (e.g., an extension that can protrude from the nanoparticle), a hinge, and/or an associative moiety.

Figure 3:
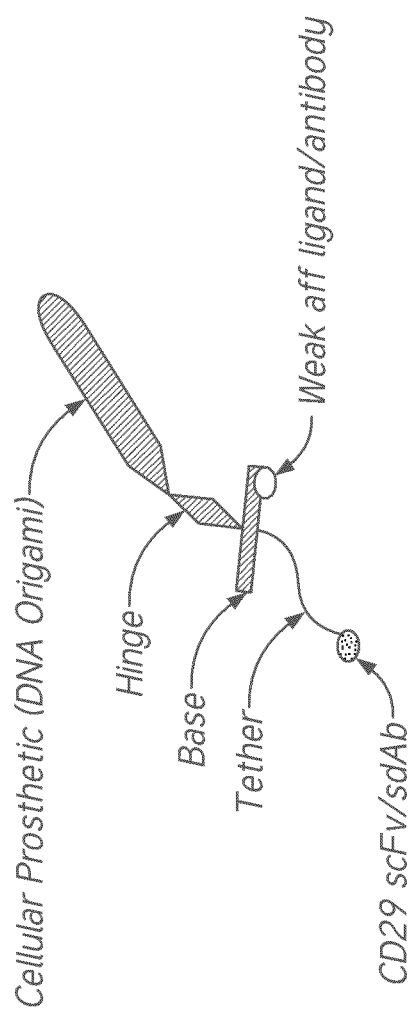
FIG. 3 shows an embodiment of targeting nanoparticle.
Figure 4:
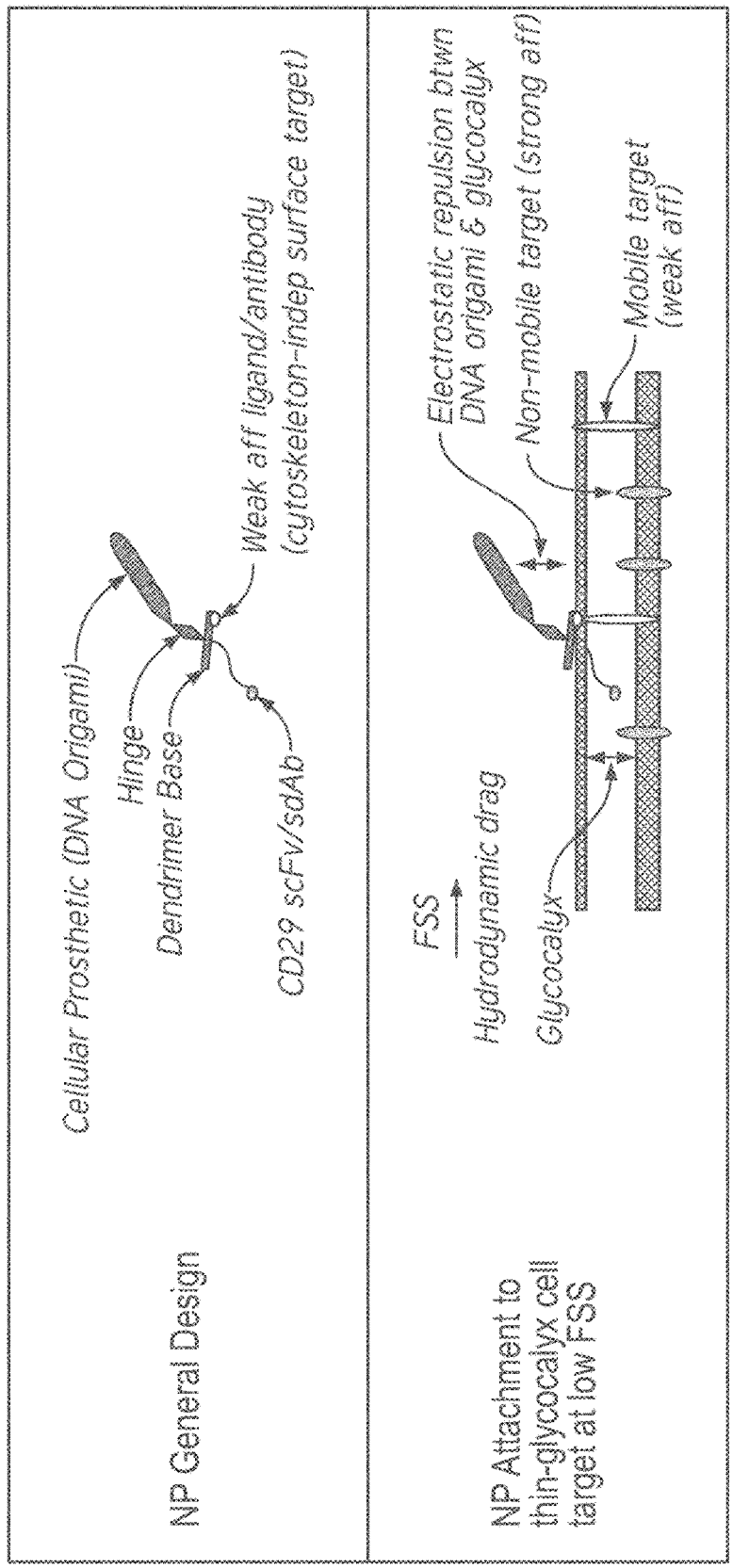
FIG. 4 shows the attachment of the embodiment of FIG. 3 to a cell.

As shown in FIG. 3, the nanoparticle probe can comprise one or more of a cellular prosthetic, a hinge region, a base structure with a weak affinity ligand (e.g., an antibody), a tether, and an associative moiety (e.g., CD29, scFv, sdAb, etc.). In some embodiments, the nanoparticle probe does not comprise one or more of the cellular prosthetic, hinge region, base structure with a weak affinity ligand (e.g., an antibody), tether, and/or the associative moiety (e.g., CD29, scFv, sdAb, etc.). In some embodiments, as shown in FIGS. 3 and 4, the base comprises a weak affinity ligand (e.g., a slip bonding moiety, etc.). In some embodiments, the slip bond allows the nanoparticle probe to attach and detach from cells. In this way, the slip bond allows the stronger binding associative moiety to bind to the cell surface where, for instance, the tether is of sufficient length to penetrate the glycocalyx completely. Thus, the nanoparticle probe can reversibly bind via the slip bond until it reaches a particular cell where the glycocalyx has an appropriate depth to allow the associative ligand to bind. As shown in FIG. 4, where the nanoparticle nanoprobe binds to a portion of the glycocalyx in a manner that the associative moiety (e.g., the CD29, scFv, sdAb, irreversible binding agent, etc.) does not contact its target cell surface marker, the slip bond will eventually release the nanoparticle probe to bind to another cell. In some embodiments, the slip bond allows flow through the plasma (or another biological medium) until the nanoparticle probe associative moiety binds to a cell surface. In some embodiments, the associative moiety binds strongly to a particular, pre-selected cell surface ligand based on the target cell marker that is expressed, thereby targeting a particular diseased cell (for diagnosis or delivery of a therapeutic). In some embodiments, as discussed elsewhere herein, the slip bond forms a transient bond that allows the associative moiety to bind to the cell surface depending on the length of the tether. In some embodiments, the slip moiety can act as a targeting and/or binding portion of the nanoparticle probe. In some embodiments, the associative moiety forms irreversible bonds to a cell target feature.

Figure 5A:
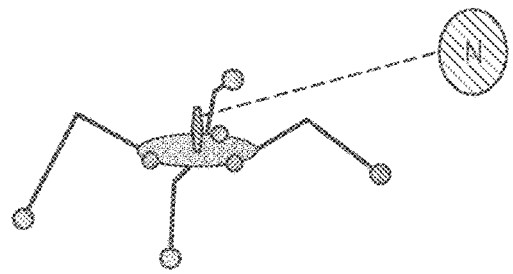
FIGS. 5A-C show another embodiment of a targeting nanoparticle.
Figure 5B:
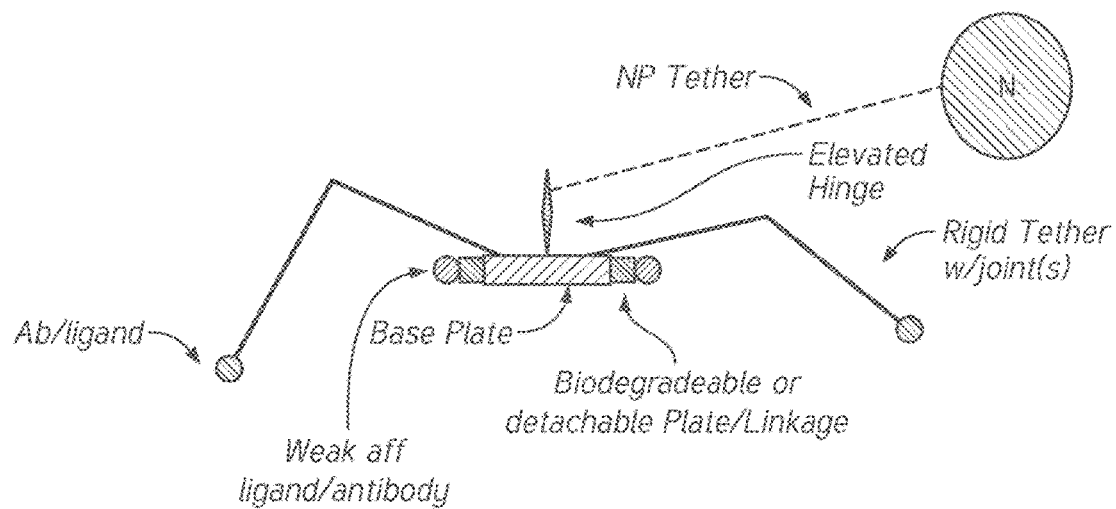
Figure 5C:
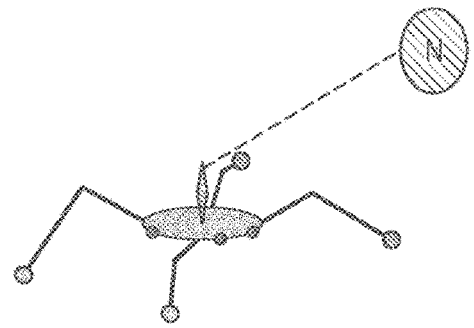

FIG. 5A-C show an alternative embodiment of a nanoparticle probe. As shown, in some embodiments, the nanoparticle probe can comprise a plurality of strong binding associative moieties (e.g., 1, 2, 3, 4, or more) coupled to the base via a plurality of tethers (e.g., 1, 2, 3, 4, or more, respectively). In some embodiments, as shown, the nanoparticle probe can comprise a plurality of slip bonds (e.g., 1, 2, 3, 4, or more). In some embodiments (not pictured) as discussed elsewhere herein, a base structure is not required and the associative moieties and slip bonds are simply located on a tether.

As shown in FIG. 5, the hinge can link the base portion to a nanoparticle group that facilitates travel and binding of the nanoparticle nanoprobe to a cell surface. In some embodiments, the hinge allows rotational freedom. In some embodiments, the nanoparticle group creates drag and/or directional orientation of the nanoparticle nanoprobe to facilitate detachment from the cell surface. In some embodiments, the cellular prosthetic (and/or nanoparticle group) creates additional drag to modulate mechanoreceptor sensitivity. In some embodiments, the hinge gives the nanoparticle probe rotational freedom and/or flexibility. In some embodiments, the hinge of FIG. 4 for example, can give the nanoparticle probe rotational freedom and/or flexibility but is conformationally restricted to prevent totally free movement about the hinge. In some embodiments, the hinge allows the cellular prosthetic to travel in the direction of fluid flow while allowing the slip bond and/or the associative bond to properly align to bind to the cell surface.

In some embodiments, the nanoparticle probe of FIG. 3 can be used for glycocalyx-dependent targeting for delivery of mechanosensors or cellular prosthetic to microvascular ECs for tissue engineering applications, in order to lower the FSS threshold of apical mechanoreceptors 'in vitro' (not in scale). FIG. 4 shows the attachment of the embodiment of FIG. 3 to a cell having a thin glycocalyx. On the figure, the tether is unlabeled, and located between a scFv/sdAb and base.

In some embodiments, the embodiment of FIG. 5A-C can be used, for example, for early in vivo imaging and delivery to microvascular ECs nearby inflamed regions (not in scale; position is relative).

In some embodiments, the nanoparticle probes described herein utilize one or more of hydrodynamic drag, slip bond behavior, tether length, convection/diffusion behavior, and changes in cell membrane fluidity in response to fluid shear stress (FSS) as a way to target cells. In some embodiments, this allows cells with a glycocalyx below a specified thickness or cells in specific FSS conditions to be targeted. In some embodiments, static or pulsed magnetic field can alter cell membrane fluidity and cell phenotype.

Due to the effect of size on hydrodynamic drag, nanoparticles are diffusion dominant, compared to microparticles that are convection dominant. In other words, the shape and size of nanoparticle probes has an effect on their biodistribution, determined by their diffusivity (i.e., Stokes-Einstein-Sutherland equation), convection-diffusion behavior (i.e., Peclet's number), and hydrodynamic drag. For instance, assuming a Peclet number (convection:diffusion)=1, in the smallest capillary (about 3 μm), in order for convection to partially dominate in the lower limits of fluid flow in a perfusion bioreactor (about 1-10 μm/sec), the nanoparticle probe can have a diameter ranging from about 20 to about 160 nm. In some embodiments, the nanoparticle probe diameter (or a largest dimension of the nanoparticle probe) is greater than equal to about: 20 nm, about 50 nm, about 100 nm, about 150 nm, about 200 nm, or ranges including and/or spanning the aforementioned values. In some embodiments, the nanoparticle probe diameter (or a largest dimension of the nanoparticle probe) is less than equal to about: 20 nm, about 50 nm, about 100 nm, about 150 nm, about 200 nm, or ranges including and/or spanning the aforementioned values. Since some embodiments of the targeting technology incorporate glycocalyx surface slip bonds and tethering across the glycocalyx, the hydrodynamic drag is characterized by two different states, which can be characterized by computational modeling of nanoparticle probes in free flow, prior to binding, and of tethered objects near surfaces, after binding to a surface. In some embodiments, the targeting feature simulates a convection-dependent and glycocalyx-thickness-dependent biodistribution within a biological system.

In some embodiments, as mentioned above, the nanoparticle does not comprise one or more of a base/scaffold structure, a tether, a hinge, or an associative moiety. For instance, in some embodiments, a series of tethers, as discussed elsewhere herein, are bound together at a nucleus without a nanoparticle core. In some embodiments, single functionalized tether can operate as the nanoparticle probe. In some embodiments, the tether is not present and associative moieties are bound directly to a hinge or a nanoparticle to provide a nanoparticle probe. Any combination is envisioned of nanoparticles, tethers, hinges, and associative moieties is envisioned.

In some embodiments, by virtue of any one of shape, physical properties, electrostatic properties, and/or targeting ligands, a nanoparticle probe can target a cell. In some embodiments, the nanoparticle shape can be selected based on its hydrodynamic drag in flow ranges of interest. In some embodiments, the nanoparticle's on-off binding within capillary pulsatile flow ranges, with attachment below a FSS threshold of interest, is used for flow-dependent microvascular targeting and assessment of microvascular perfusion to study disease models or shift in environment, states, or other stimuli.

In some embodiments, the nanoparticle and/or nanoparticle probes can be generally and/or substantially spherical in shape, rod-shaped, disc-shaped, cube-shaped, or otherwise. In some embodiments, the nanoparticle probe can have a flat or low curvature base structure that can be used. In some embodiments, the length is of a certain ratio to the height or width of the nanoparticle probe. In some embodiments, the length and width of the nanoparticle probe have a ratio wherein the ratio is greater than about 1.5:1, about 2:1, about 3:1, about 4:1, about 5:1, ratios ranging between two of the aforementioned ratios, or otherwise. In some embodiments, the length and height of the nanoparticle probe have a ratio wherein the ratio is greater than about 1.5:1, about 2:1, about 3:1, about 4:1, about 5:1, ratios ranging between two of the aforementioned ratios, or otherwise.

In some embodiments, the materials of the nanoparticle (e.g., the base-structure, the cellular prosthetic, the hinge, nanoparticle group etc.) can be selected to prevent penetration through glycocalyx (e.g., hydrophobic, anionic, etc.). In some embodiments, the nanoparticle (or nanoparticle probe) comprises one or more materials be selected to associate to the cell surface. In some embodiments, the nanoparticle comprises one or more of DNA and/or RNA origami or another nanomaterial (e.g., a paramagnetic nanoparticle, quantum dot, nanocrystal). In some embodiments, the nanoparticle base structure comprises one or more of gold or iron-oxide core nanoparticle or other nanoparticles, not limited to single-chain polymer nanoparticles (e.g., PEG, PGA, PGA-g-PEG, PLA, PLGA, etc., having molecular weights of at least about: 10,000 g/mol, 100,000 g/mol, 200,000 g/mol, or ranges spanning the aforementioned values) and poly(amidoamine) (PAMAM) dendrimers. In some embodiments, the nanoparticle base structure comprises one or more of colloidal gold, TNF-bound colloidal gold, albumin (or other similar biomolecules), dendrimeric poly(l-lysine), dendrimeric poly(l-lysine) which presents anionic, naphthalene disulphonate surface groups, dendrimeric polypropylenimine (PPI), Denkewalter-type PLL dendrimer, Tomalia-type PAMAM dendrimer, hydroxylated PAMAM dendrimer, Hult-type poly(ester) (bis-MPA) dendrimer, Majoral/Caminadetype phosphorous-based dendrimer, Simanek-type triazine based dendrimer, Jayaraman/Jain-type poly(propyletherimine) (PETIM) dendrimer, PEG-PLL, PEG-PAMAM, PETIM-DG, PEG-PPI, peptide dendrimer conjugate, and polystyrene latex particles.

In some embodiments, the nanoparticle probe comprises a neutral or negative zeta potential. In some embodiments, the nanoparticle probe comprises a fluorophore or other functional component.

In some embodiments, the particle size (e.g., a diameter of the particle, a largest dimension of the particle, etc.) of the nanoparticle probe (or microparticle probe as the case may be) is less than about 10 µm, about 5 µm, about 1 µm, about 900 nm, about 800 nm, about 700 nm, about 600 nm, about 500 nm, about 400 nm, about 300 nm, about 200 nm, about 100 nm, about 50 nm, about 25 nm, about 10 nm, ranges spanning the aforementioned values, or otherwise.

In some embodiments, as discussed elsewhere herein, the base structure can be functionalized with slip bonds to allow increased binding affinity of the associative moiety. In some embodiments, the slip bonds allow increased binding affinity of the associative moiety due to increased residency time for the binding of the associative moiety. In some embodiments, reversibly associative moieties—those capable of forming slip bonds (e.g., low-affinity antibodies with $K_d > 10^{-7}$ M or ligands)—are functionalized (e.g., covalently, through binding, coupling, complexation, hydrophobic/hydrophilic interactions, ionically, etc.) to the base (e.g., a nanoparticle) to target cells. In some embodiments, binding affinity can be increased by multivalency (as shown in FIG. 5, for example). In some embodiments, a tether binds the slip bond to the nanoparticle probe, while in other embodiments, a tether is not used. In some embodiments, slip bonds (e.g., low affinity antibodies or ligands that have a bind strength below about 100 pN) function as a targeting moiety for temporary binding of nanoparticle probe to a glycocalyx surface target. In some embodiments, slip bonds or non-slip bonds bind to secondary mobile targets on the surface of the glycocalyx. In some embodiments, these slip bonds associate to the surface in low (0.05-1 dyne/cm$^2$) or moderate (10 dyne/cm$^2$) FSS conditions. In some embodiments, the slip bonds dissociate in high (>10 dyne/cm$^2$) FSS conditions. In some embodiments, slip bonds or another targeting modality for binding to secondary target(s) on glycocalyx surface where increased binding efficiency is desired are used. In some embodiments, the non-slip bonds or higher affinity bonds (e.g., the associative moieties) are used as a permanent or higher duration targeting moiety. In some embodiments, non-slip bonds or higher affinity bonds are used in glycocalyx-thickness-limiting tethers or other component. In some embodiments, the nanoparticles or nanoparticle probes are targeted using selectins such as PECAM, VCAMs, and ICAMs and integrins such as CD11/CD18 functionalized to the surface of the nanoparticle. In some embodiments, a nanoparticle (DNA and/or RNA origami for example) can be patterned with either small molecules, antibodies, or larger proteins. In some embodiments, they are patterned with RGD peptides, anti-ICAM VHH antibodies, or sialyl Lewis X.

In some embodiments, the material selected for incorporating or generating a slip bond can comprise one or more of an binding motif, a DNA and/or RNA, a dendrimer, or another polymers/nanomaterials with a neutral or negative zeta potential for the base (i.e., base plate). In some embodiments, the material can be of any shape. In some embodiments, the material is spherical, rod-shaped, disc-shaped, cube-shaped, or otherwise. In some embodiments, the material is a position-limited shape (e.g., flat or low curvature on attachment site) to control the orientation or position of the attached nanoparticle. In some embodiments, the slip bonds include a hyaluronan targeting motif, chondroitin sulfate targeting motif, dermatan sulfate targeting motif, heparan sulfate targeting motif or other glycocalyx surface EC targeting motifs. In some embodiments, the slip bond are lectin-binding proteins such as recombinant CD44, bounded to the material covalently or by specific binding groups (biotinylation or oligonucleotide conjugation at the C or N terminus).

In some embodiments, the slip bond moiety can be formed using one or more of a carbohydrate-based ligand (sialyl Lewis X) or low-affinity antibody isolated via chromatography. In some embodiments, the binding strength of the slip bond moiety is below about 500 pN, about 100 pN, about 50 pN, about 10 pN, about 5 pN, ranges spanning those values or otherwise. In some embodiments, the binding strength of the slip bond moiety is at least about 0.5 pN, about 1 pN, about 5 pN, ranges spanning those values or otherwise. In some embodiments, the slip bond is formed in conjunction with a cytoskeletal-independent (i.e., mobile) target on the cell's glycocalyx surface. In some embodiments, the dissociation constant of the slip bond moiety is at least about $10^{-3}$ M, which is around the dissociation constant of sialyl Lewis X to E-selectin (878 µM). In some embodiments, the binding strength of the associative moiety is at least about 2000 pN, 1000 pN, 500 pN, about 100 pN, ranges spanning those values or otherwise. In some embodiments, the dissociation constant of the associative moiety is at least about those of strongly binding antibodies, whose dissociation constants range from $10^{-13}$ to $10^{-7}$ M. Without being bound to any particular mechanism, it is believed that the hydrodynamic drag force on the nanoparticle can cause its dissociation at higher flow rates, and fluid shear stress increases cell membrane fluidity (affects mobile component). In some embodiments, this feature modifies the nanoparticle to become more convection-dependent. In some embodiments, increased binding time at low flow rates increases the binding efficiency of the tether, if within the target thickness threshold.

In some embodiments, slip bonds that dissociate under increased FSS (e.g., above about more than 1 dyne/cm$^2$, with a binding strength below 50 pN (which is the hydrodynamic drag at which Brownian motion is negligible for a microparticle) are used to fabricate the nanoparticle probe. In some embodiments, the slip bond (e.g., weak affinity antibody or ligand) dissociates at higher FSS and increases binding time at lower FSS (pulsatile).

In some embodiments, the slip bond comprises a biodegradable or detachable section for eventual isolation of tethered prosthetic construct. In some embodiments, this isolation allows removing untethered nanoparticles that are bounded to its target solely by slip bonds, due to low FSS environment relative to target. In some embodiments, linkage of additional tether(s) to other functional products (e.g., enzymes, drugs, ligands, imaging agents (e.g., dyes), bases for self-assembly nanoparticles, tissue engineering initiators) can be performed.

In some embodiments, for example, where a base structure is not used, slip bonds may be placed between spacing of tethers. In some embodiments, slip bonds may be placed between spacing of tethers where a base structure is used.

As stated above, tethers can be used in addition to or instead of nanoparticle probe base structures. In some embodiments, as discussed elsewhere herein, a tethered nanoparticle group induces hydrodynamic drag in flow conditions (see FIG. 5). In some embodiments, the tether acts as a targeting moiety for binding to a primary target on a cell surface. In some embodiments, the tether acts as a targeting moiety for binding to a primary target on a cell surface through a glycocalyx below a specified thickness, whose attachment is limited by tether length. In some embodiments, tethers function as spacers between the slip bond moiety and the nanoparticle core.

In some embodiments, a tether can have variable dimensions. In some embodiments, the diameter of the tether, for instance, varies by target. In some embodiments, if targeting ECs, diameter can be selected to be less than about 18 nm to penetrate the glycocalyx. In some embodiments, the diameter can be selected to be less than about 50 nm, about 25 nm, about 20 nm, about 15 nm, about 10 nm, about 5 nm, ranges spanning the aforementioned values, or otherwise to, for instance, penetrate glycocalyx. In some embodiments, the diameter is about 18 nm, to penetrate glycocalyx based on the distance between carbohydrate brush structures of the glycocalyx. In some embodiments, the length of the tether can vary. In some embodiments, the length varies by target. In some embodiments, if targeting microvascular ECs of capillaries, the total tether length can be between about 20-200 nm. In some embodiments, the tether length is below about 400 nm, about 300 nm, about 200 nm, about 100 nm, about 50 nm, about 25 nm, about 10 nm, ranges spanning the aforementioned values, or otherwise. In some embodiments, the length is sufficient to reach and bind to a cell surface target through the targeted cell's glycocalyx.

In some embodiments, where the tether is functionalized to a base structure, the spacing of the tether on the nanoparticle can be varied. In some embodiments, spacing between carbohydrate complexes or glycans in ECs are assumed to be ubiquitously 20 nm apart. Glycocalyx thickness in diseased EC capillaries ranges from 10 nm to 30 nm in comparison to the control range of 60 nm to 80 nm; however, this thickness may be an underestimation since characterization of the glycocalyx is limited by technology and technique. In some embodiments, the tethers are selected to be of sufficient length to allow binding to the cell surfaces of diseased EC capillaries and/or carbohydrate complexes or glycans in ECs.

Tether length and design can be manipulated to increase binding efficiency to the target. Compared to flexible tethers, controlling diffusive motion on a rigid hinged tether would have a higher binding probability to a nearby target. In some embodiments, the spacing of tethers on, for example, the nanoparticle probe base varies by target. In some embodiments, the spacing is at least about 1 tether/10 nm$^2$, about 1 tether/50 nm$^2$, about 1 tether/100 nm$^2$, about 1 tether/200 nm$^2$, about 1 tether/300 nm$^2$, about 1 tether/400 nm$^2$, about 1 tether/600 nm$^2$, or about 1 tether/800 nm$^2$. In some embodiments, if targeting ECs, the spacing is at least about 1 tether/400 nm$^2$. In some embodiments, multiple tethers can be used together on a single nanoparticle probe. In some embodiments, for 2 µm microparticles and 500 nm nanoparticles, has significantly smaller spacing and shorter tether length. In some embodiments, the overall adhesion of the nanoparticle can be 4-17 fold lower than the microparticles, which may be significantly enhanced by this invention via slip bonds. In some embodiments, if multiple tethers are used, spacing (<1 tether/400 nm$^2$) above glycocalyx surface can be selected to penetrate glycocalyx.

In some embodiments, the tethers are functionalized at the distal end of tether (scFv or other) to bind against primary target of interest near cell membrane (receptors of interest, such as selectins and integrins, are ~11 nm above membrane).

In some embodiments, the material selected for use as a tether can comprise one or more of DNA and/or RNA, a glycan, a lipid, a glycolipid, a proteoglycan, or other polymers/nanomaterials. In some embodiments, the material selected is a recombinant viral tail fiber or a synthetic polymer that mimics its properties. In some embodiments, the tether can comprise polyethylene glycol (PEG) having a molecular weight below about 500 Da, 1000 Da, 3000 Da, 10000 Da, etc. In some embodiments, the material is neutral in charge. In some embodiments, the tether has a core structure(s) that is rigid. In some embodiments, the tether is with or without flexible joint(s) to limit diffusive movement of tether in order to maximize binding chance to cell surface target through the glycocalyx. In some embodiments, despite the negative charge of DNA origami, its penetration of the glycocalyx is successful. In some embodiments, this is due to a 15 nm×100 nm, 24 double helix bundle DNA origami rod that can penetrate HUVEC glycocalyx in static conditions.

In some embodiments, the tether comprises a targeting moiety. In some embodiments, the targeting moiety comprises one or more of an antibody, antibody fragment, ligand to cell surface receptor (ie. Sialyl Lex), aptamer, receptor, or other targeting entities.

In some embodiments, the hydrodynamic drag of tethered nanoparticles takes into account other forces such as lift or buoyancy, and tethered nanoparticles (less than about 80 nm in size) have a contradictory hydrodynamic drag of 1-2 pN at 2 mm/sec flow velocity based on a study of nanoparticles tethered to ε-toxin receptors having a measured spring constant of 0.7 pN/μM after flow. Normal blood flow velocity is greater than about 1 mm/sec in the microvascular beds, and would be much lower near the wall, with exclusion of areas near the compression for red blood cells (RBCs) which would have an increased shear rate. Mean RBC flow velocity can range from 0.2 to 0.8 mm/sec in capillaries. Furthermore, pulsatile flow exists in capillary beds. Thus, if a slip bond strength with, for instance, a binding force below about 10 pN is used, biodegradable or detachable section for isolation of tethered prosthetic construct, for the purpose of removing untethered nanoparticles that are bounded to its target solely by slip bonds, due to low FSS environment relative to target may become redundant (but this may depend on non-EC targets).

In some embodiments, the general design of glycocalyx-dependent targeting technology rely on a tethered antibody (monoclonal single-chain variable fragment) against a primary target. In some embodiments, a tether(s) of a specified length is bounded to a base structure containing slip bonds to a secondary target if higher affinity is desired, and complexed with a hinge and nanobody. In some embodiments, slip bonds dissociate under increased FSS, with a binding strength below 50 pN. In some embodiments, the nanobody of a designed shape and deformable material, will induce hydrodynamic drag (>50 pN) after temporary binding to components of the glycocalyx surface via slip bonds (~1-10 pN binding strength) under flow conditions. In some embodiments, this property provides the nanoparticle probe construct with unique convection-dependent behavior. In some embodiments, the dimensions are determined for convection to primarily dominate within a selected flow velocity range, as previously mentioned. In some embodiments, when temporarily bounded through slip bonds, the hydrodynamic drag experienced by the construct in flow conditions may be resisted by tether forces due to cell membrane fluidity. Cell membrane fluidity is associated with membrane viscosity, and FSS increases EC membrane fluidity. In some embodiments, the time between slip and release affects tethered antibody binding chance to cells below a glycocalyx-thickness threshold. In some embodiments, this slip-bond feature simulates flow-dependent targeting in the nano-scale. However, in some embodiments, non-specific binding will occur near static regions if hydrodynamic drag is insufficient to break the slip bonds. In some embodiments, the number and spacing between tethers can be determined.

Figure 12B:
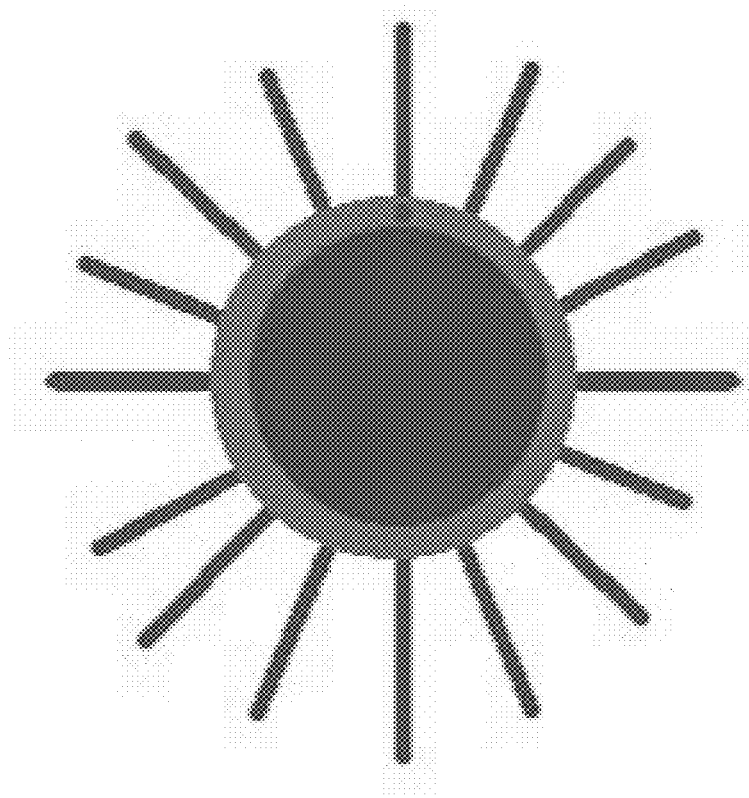
FIGS. 12A and 12B shows an embodiment of a targeting nanoparticle with tether length that changes over time.
Figure 12A:
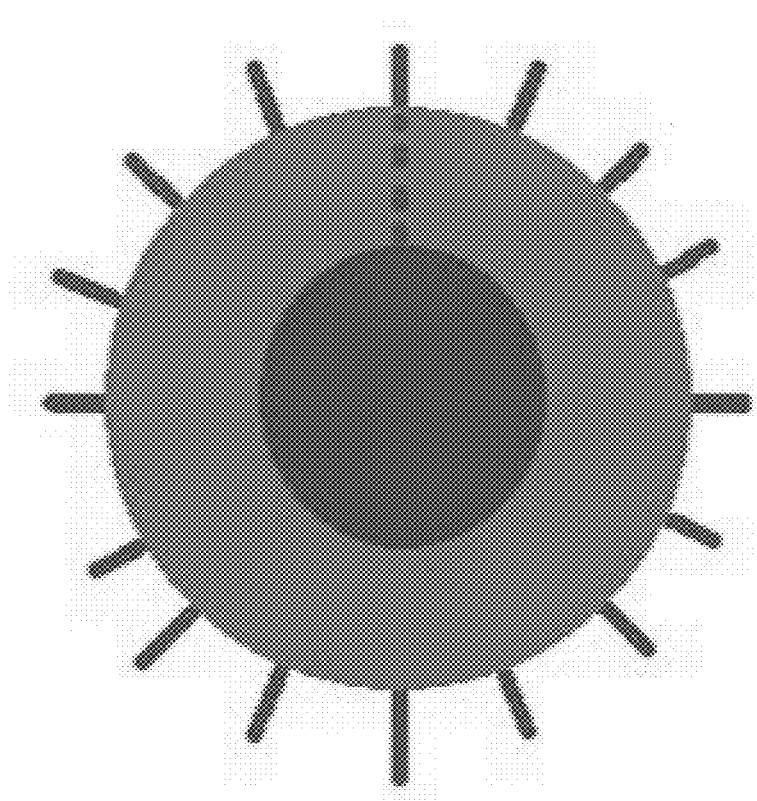

FIGS. 12A and 12B show an embodiment of a nanoparticle probe with tether length that varies over time. In some embodiments, as shown in FIG. 12A, the nanoparticle probe has a core that is coated with a biodegradable layer. In some embodiments, as the outer biodegradable layer thins over time, the tethers become more exposed (as shown in FIG. 12B), and length of the tethers relative from the surface is increased. In some embodiments, the tethers are encapsulated by a biodegradable material to achieve this change. In some embodiments, the biodegradable material is comprised of one or more of poly-D-L-lactide-co-glycolide, polylactic acid, poly-ε-caprolactone, chitosan, gelatin, or poly-alkylcyanoacrylates. In some embodiments, this degradation and exposure allows the nanoparticle probe to initially bind to cells with a severely degraded glycocalyx (e.g., via a short tether). Later, after some degradation, the nanoparticle probe is able to bind to cells with a moderately degraded glycocalyx. In some embodiments, the encapsulating material surpasses the length of the tether, or partially encapsulates the length of the tether. In some embodiments, this negates the need for designing multiple nanoparticle probes with a specific tether length for adjustment in detection. In some embodiments, time-lapse imaging can be used to map out region-specific severity or accessibility to a cell surface by tether length.

Figure 6A:
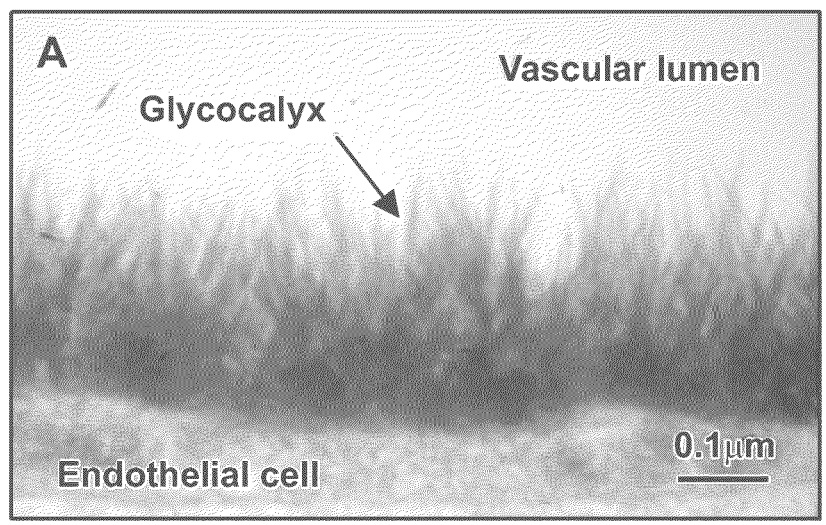
FIG. 6A-C show electron microscope images of EC glycocalyx and shedding.
Figure 6B:
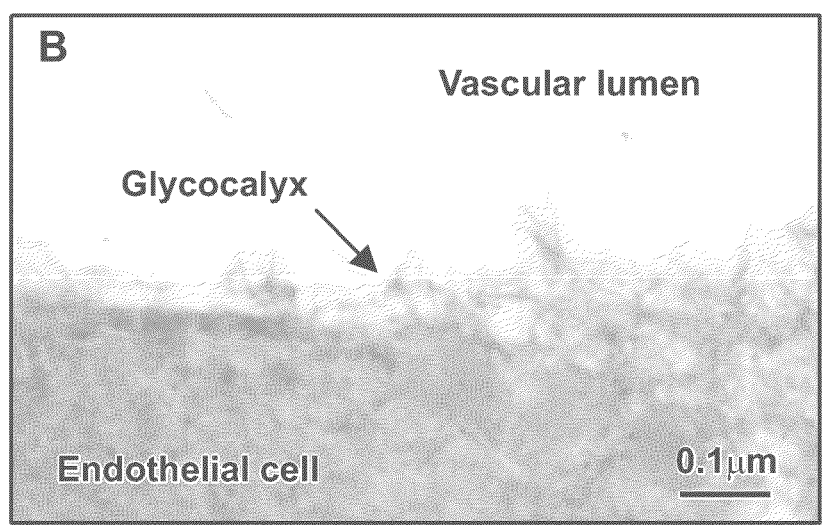
Figure 6C:
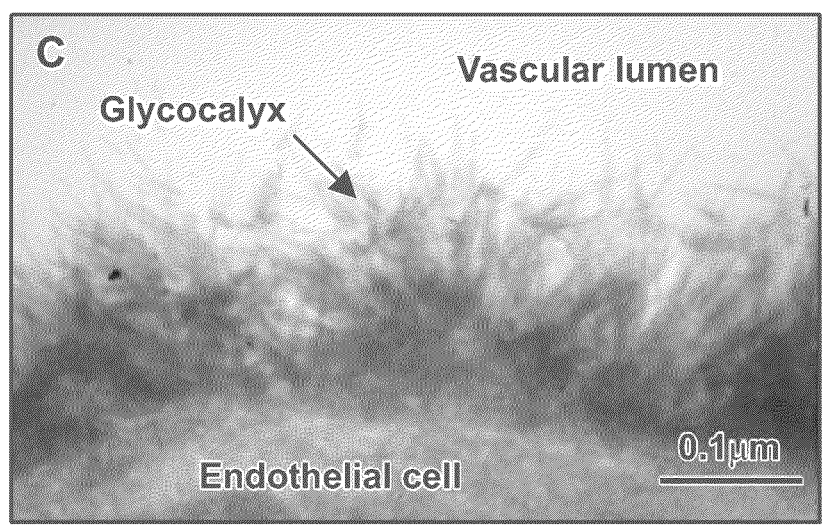

FIG. 6 shows electron microscopic views of the hearts stained to reveal the glycocalyx. (A) An intact glycocalyx after 20 min of perfusion (Group E) and (B) the nearly completely degraded endothelial glycocalyx after 20 min of warm ischaemia and consecutive reperfusion (Group A). (C) The glycocalyx after pre-treatment with antithrombin and 20 min of warm ischaemia and reperfusion (Group B). The endothelial glycocalyx is mostly intact. In some embodiments, the nanoparticle probes disclosed herein can be varied to target any one of the glycocalyx structures of FIGS. 6A-C to the exclusion of or together with the others.

In some embodiments, as discussed elsewhere herein, the nanoparticle can be attached to a hinge component. In some embodiments, the attachment of nanoparticle to a hinge above glycocalyx allows (or facilitates) computational modeling of hydrodynamic drag of tethered nanoparticles. In some embodiments, this modeling is for future modifications of the construct. Nanoparticle groups may be elevated above the base portion of the nanoparticle probe via hinge to facilitate computational modeling for future modifications. For in vivo applications, in some embodiments, the length of the nanoparticle probe tether and hinge accounts for compression by RBCs on the entire component, which may be addressed by distance to the base during compression. Shape and surface properties of the nanoparticle probe may be modified to alter hydrodynamic drag based on the application.

In some embodiments, the nanoparticle groups (as shown in FIG. 5A-C) are used as a scaffold for targeting cells. In some embodiments, for example, a nanoparticle or nanoconstruct is selected based on its hydrodynamic drag properties. In some embodiments, these reversible binders can be functionalized to a nanoparticle by one or more tethers. In some embodiments, functionalized tethers of a specific length or dimension are selected. In some embodiments, the selection of a tether is based on its ability to restrict binding to cells with a glycocalyx below a certain thickness (or that have some other targetable quality). In some embodiments, the selection of a tether is based on its ability to bind to a primary target.

In some embodiments, the hydrodynamic drag of a nanoparticle that is attached to a base structure, which increases binding affinity for the nanoparticle. The design of the embodiment varies based on the application.

In some embodiments, drag forces of interest include those that are at least about 500 pN, about 100 pN, about 50 pN, about 10 pN, about 5 pN, ranges spanning those values or otherwise. In some embodiments, the drag force of interest include is at least about 50 pN for most physiological flow rates. In some embodiments, the hydrodynamic drag of the nanoparticles disclosed herein varies by distance to a surface of the cell, due to introduction of other forces such as lift.

In some embodiments, computational modeling for tethered cells can be performed, but this modeling is not applicable to nanoparticles. However, in some embodiments, a 30-50 nm diameter nanoparticle have 1-2 pN hydrodynamic drag at 0.2 cm/s. Using alternative materials, such as DNA origami (patented by Harvard) for its hydrophilicity and electrostatic repulsion against the glycocalyx, has not been attempted to my knowledge.

In some embodiments, design parameters are based on the probe's hydrodynamic drag, slip-bond strength, and convection-diffusion behavior. In some embodiments, prior to conducting complex studies within a living body, the nanoparticle probe is designed in a way to allow it to be modeled outside the body in a simple yet alternate application—resolving a limitation in tissue engineering. To address insufficient cell growth in areas of slow media flow that occurs even with sufficient nutrients, mature vessels will be stabilized in low flow conditions, and vessel sprouting will be stimulated in near static regions. This can be achieved within a large scaffold through delivery of mechanosensor prosthetics to endothelial cells (cells lining the blood vessels) located in low flow conditions and characterized by a thin glycocalyx. In some embodiments, cell surface modification will lower the mechanical threshold at which cells sense fluid flow in their surrounding environment, which creates a shift in the physiological development of blood vessels. In some embodiments, a more robust pre-vascularized construct can be developed, thereby addressing a limiting factor in the engineering of various tissues.

Some embodiments pertain to developing a targeting technology on microvascular endothelial cells. In some embodiments, the technology can be used in a simple 2-D cell culture flow model, under several flow conditions and simulated pathophysiological states. In some embodiments, testing can then be conducted in a complex 3-D flow model as a pilot study for further investigation.

In some embodiments, the nanoparticle probes described herein have application in the fields of theranostic nanomedicine, regenerative medicine, tissue engineering, and basic research in mechanotransduction. In some embodiments, the nanoparticle probes allow users to explore biological mechanisms that occur during the remission of non-communicable chronic diseases, the leading cause of death and disability in the United States. In some embodiments, this approach can lead to the advent of novel diagnostic methods and therapies. In some embodiments, the nanoparticle probes can be used in a method of diagnosing non-communicable chronic disease and/or the stage of progress of that disease. In some embodiments, the nanoparticle probes can diagnose "at risk" individuals prior to that patient showing symptoms of the disease. In some embodiments, the nanoparticle probes can be used to develop treatment strategies and therapeutic regimens for patients. For example, in some embodiments, the nanoparticle probes can be used to determine if a particular treatment regimen is suitable (e.g., diet and exercise versus drug treatment, etc.). There is an association between microcirculatory dysfunction in the development and pathogenesis of various chronic diseases, including diabetes, hypertension, end-stage renal disease, osteoporosis, and other chronic conditions. However, there is no robust strategy to target or monitor subtle early changes in deep tissue regions with poor microcirculatory status for measuring intervention outcome in translational research. In some embodiments, the nanoparticle probes described herein can be used in theranostic nanomedicine.

FSS induces glycan synthesis in ECs, and the EC glycocalyx is degraded in inflammatory conditions, especially in diabetes. FSS induces glycan synthesis in ECs, yet FSS also causes glycocalyx shedding, thereby counteracting each other to establish a balance. The EC glycocalyx functions as a mechanosensor that detects the surrounding FSS and is capable of adaptive remodeling over time. Thus, in some embodiments, controlled targeting of ECs characterized by a degraded glycocalyx in low FSS by the nanoparticle probes disclosed herein has a variety of potential applications.

In some embodiments, the nanoparticle probes can be used to lower the FSS detection threshold of mechanoreceptors. In some embodiments, increasing the hydrodynamic drag force experienced by mechanoreceptors, such as integrins (e.g., β1 Integrin subunit), syndecans, primary cilia, and other mechanosensors, has various biomedical applications (e.g., in tissue engineering). In some embodiments, the β1 Integrin subunit (CD29) in ECs is characterized by deglycanated mechanoreceptor complexes. FSS-induced CD29 is involved in various signal transductions, including elongation, angiogenic signaling, and EC reorientation of cardiomyocytes. Vascular endothelial growth factor (VEGF) and FSS plays a synergistic role in capillary morphogenesis, and FSS attenuates sprouting while VEGF gradients direct sprouting. Lowering the FSS detection threshold of CD29 in apical ECs would stabilize mature vessels in lower FSS regions and stimulate sprouting in near-static regions, potentially yielding a more robust prevascularized in vitro 3D construct for tissue engineering applications. DNA origami is a potential prosthetic material, due to electrostatic repulsion to the glycocalyx, its biodegradability by nucleases prior to tissue transplantation to avoid immunogenicity, and non-toxicity if intracellularized with its target and degraded by lysosomes. In some embodiments, the nanoparticle probes can be used for tissue engineering strategies. In some embodiments, the nanoparticle probes can be used for vascular development for to various tissues, such as the bone, heart and other organs and or for tissue development of bone, heart and other organs/tissues. The development of a robust prevascularized construct remains a limiting factor on sufficient stem cell growth within the core of large scaffolds and other matrices in top-down approaches of tissue engineering. In some embodiments, the nanoparticle nanoprobes allow targeted vascular development and growth. In some embodiments, one or more agents bound to the nanoparticle nanoprobe include VEGF, angiopoietins, or FGF.

The vascular endothelium is an early site of damage during inflammation. Thus, in some embodiments, using the nanoparticle probes could allow the preservation of the endothelial surface layer of microcirculatory vessels under microvascular dysfunction and could reduce damage caused by either chronic low-grade inflammation or reperfusion. In some embodiments, the nanoparticle probes could detect and or target an area of disease leading to the diagnosis and treatment of the disease using the nanoparticle probe as a delivery agent for, for instance, pharmaceuticals or other small molecules. As a diagnostic agent, the nanoparticle probe can be used to indicate early patient pathology and can be used to develop a treatment regimen (e.g., medicines/supplements to be used, dietary changes, exercise regimens, etc.). In some embodiments, adverse effects on physiological processes can be limited or avoided if the nanoparticle design (tether length) limits its binding to cells below a specified glycocalyx thickness of interest.

In some embodiments, FSS-induced CD29 in ECs is involved in various signal transductions, including elongation, angiogenic signaling, and EC reorientation of cardiomyocytes. Vascular endothelial growth factor (VEGF) and FSS play a synergistic role in capillary morphogenesis, and FSS attenuates sprouting while VEGF gradients direct sprouting. In some embodiments, lowering the FSS detection threshold of CD29 in apical ECs would stabilize mature vessels in lower FSS regions and stimulate sprouting in near-static regions, potentially yielding a more robust prevascularized in vitro 3D construct for tissue engineering applications.

In some embodiments, other mechanotransduction-based studies and additional applications may be obtained through other modifications including attachment of enzymes or other prosthetics to alter mechanoreceptor properties or other cell functions, and these cellular targets would not be limited to ECs. There are over 300 cell types in humans. In some embodiments, markers of any one of these cells can be targets of the ligands of the nanoparticle probes disclosed herein. In some embodiments, in vitro applications can be established to refine the nanoparticle probe targeting technology for conducting in vivo research of various animal disease models.

In some embodiments, the nanoparticle probe utilizes one or more of hydrodynamic drag, slip bond behavior, tether length, convection/diffusion behavior, and changes in cell membrane fluidity in response to fluid shear stress (FSS), in order to target cells below a specified glycocalyx thickness and in low FSS conditions. The association between low basal chronic inflammation to low FSS and glycocalyx degradation in ECs is an early pathophysiological indicator. In vitro applications can be initially established as a blueprint, prior to conducting in vivo research. In some embodiments, the nanoparticle probes can be used to validate the design parameters of model systems for an in vitro study. In some embodiments, the nanoparticle probe and systems using the same can accomplish at least the following specific aims: 1) Developing a Design in a 2-D Cell Culture Flow Model and 2) Validating Design in a Perfusion Bioreactor.

These aims can be accomplished by validating the nanoparticle probe's targeting properties (FSS/glycocalyx thickness-dependent targeting) and its functional modification (targeted delivery of mechanosensor prosthetics on the cell surface) for potential tissue engineering applications. In some embodiments, the approach involves conducting experiments in a microbioreactor under different flow rates of cell media and pathophysiological conditions that affect glycocalyx thickness. In some embodiments, the nanoparticle probe can be used to lower the mechanical threshold at which microvascular endothelial cells sense fluid flow in their surrounding environment. In some embodiments, this is achieved through attachment of a prosthetic molecules to an epitope of interest on a mechanoreceptor. In some embodiments, the nanoparticle probes could be used to experimentally validate the induced phenotypic changes and the targeting properties of the nanoparticle probe. In some embodiments, this is achieved through measurement of intracellular metabolites or indicator dyes. In some embodiments, testing systems and use of nanoparticle probes with glycocalyx-thickness and FSS-dependent targeting properties can be developed. In some embodiments, testing systems are organs-on-chips.

In some embodiments, the nanoparticle probes can be used to address insufficient cell growth in areas of low flow that occurs even with sufficient nutrients by improving vascularization techniques in large scaffolds. In some embodiments, this is achieved through delivery of mechanosensor prosthetics. Experiments in perfusion bioreactor co-culture under different flow rates can be performed to control biodistribution. The nanoparticle probes could be used to experimentally validate stabilized mature vessels in low flow conditions and vessel sprouting in near static regions. Changes can be associated with a 3-D flow profile, with velocimetry techniques. In some embodiments, testing systems and use of nanoparticle probes could identify areas where this technology could be used to address limitations in tissue engineering. In some embodiments, cell types are tested for potential glycocalyx-thickness-dependent targetability or for differences in glycocalyx surface targets or characterization.

In some embodiments, the nanoparticle probes could be used in tissue engineering design. For instance, in some embodiments, such as bone tissue engineering, perfusion bioreactors could be used. Perfusion bioreactors have improved the mass transfer of nutrients and growth of FSS-dependent stem cells seeded in bone scaffolds. Perfusion bioreactors are typically characterized as a closed system containing one or more tissue constructs, and having an inlet and outlet for media flow.

For in vitro applications, control of mechanical stimulation is lacking in larger 3D cell culture constructs. Despite improvements, cellular density near the core is less than the periphery. Flow variability from frictional loss within bioreactors may lead to insufficient growth in areas of low FSS, even with sufficient nutrients. In other cases, insufficient nutrients will result in a necrotic core. While various advancements have been made in bone tissue engineering, such as magnetic composite scaffolds and vascularization techniques, that address these various problems, there remains much room for improvement to fully address current challenges in tissue engineering. Tissue engineering strategies for vascular development can be applied to other tissues, including the heart, and other organs (kidney, liver, lung, intestines, pancreas, stomach, etc.). The development of a robust prevascularized construct remains a limiting factor on sufficient stem cell growth within the core of scaffolds and other matrices in tissue engineering.

In some embodiments, strategies in diagnostic imaging to determine microcirculatory status can be performed using nanoparticle probes. In some embodiments, as discussed elsewhere herein, the nanoparticle probes can be used in in vivo applications. The development of chronic pathophysiology may be a result of an imbalance between the amount of damage and the rate at which the damage is addressed, e.g. removal of insult by leukocytes and repair by stem cells. In addition to mesenchymal stem cells (MSCs), these stem cells include endothelial progenitor cells (EPCs) deriving from the bone marrow that are overall responsible for vascular repair and maintains the integrity of the microcirculation especially through physical exercise. FSS and cytokines interact to control the concentration of E-selectin surface expression in ECs. Damage to endothelium can be associated with an increase in circulating ECs from EC denudation or glycocalyx shedding due to very high FSS or other insults. Endothelial damage is also associated with a degraded EC glycocalyx in low FSS regions from inflammation that results in increased intravascular adhesion by leukocytes and platelets. However, the glycocalyx maintained in postcapillary EC venules are even thicker in low FSS and inflammation. The ability to visualize or target capillary regions with early indications of poor microcirculatory status using the disclosed nanoparticle probes, could be used as a theranostic tool in a variety of chronic disease animal models. In some embodiments, nanoparticle probes with an affinity for low FSS conditions and thin glycocalyx would improve upon the sensitivity of potential vascular preclinical detection methods, such as glyconanoparticles in neuroinflammation. In some embodiments, the pericyte/endothelial interface is of interest.

Glycocalyx thickness in diseased EC capillaries ranges from 10 nm to 30 nm in comparison to the control range of 60 nm to 80 nm. Technology to deliver functional nanoparticle probes to cells in low FSS within a certain glycocalyx-thickness threshold have various applications, including, but not limited to: diagnostic imaging (e.g., of microcirculatory status), delivery of nanoparticles for therapeutic effects in areas of microcirculatory dysfunction, and delivery of mechanosensor prosthetics to lower FSS detection by mechanoreceptors.

In some embodiments, imaging modalities or other non-invasive alternatives could be developed or incorporated. Current vascular imaging technologies include PET, SPECT, MRI, intravascular ultrasound, and optical imaging via optical coherance tomography or near-infrared (NIR) fluorescence. Fluorescence molecular tomography (FMT) is a form of 3-dimensional imaging of NIR fluorescent probes capable of deep-tissue visualization and early disease or biomarker detection via targeted approach, compatible with smart probes. In some embodiments, the nanoparticle probe can be functionalized with one or more dyes or radio opaque agents for visualization. In some embodiments, the nanoparticle probe can be functionalized with one or more of dyes including but not limited to indocyanine green (ICG), methylene blue, Cy5.5, ZW800-1, and IRDy 800CW. In some embodiments, the nanoparticle probe described herein could be functionalized with FMT agents. Complementing other modalities, FMT of degraded EC glycocalyx of capillaries in low FSS would serve as a generalized yet sensitive inflammatory indicator of early pathogenesis in nearby tissues, which carries a diagnostic advantage over current approaches in development that have a smaller disease spectrum due to disease-specific targets. In some embodiments, NIR quantum dots (QDs) and other dyes or proteins, capable of deep-tissue visualization and early disease or biomarker detection can be implemented in the targeted approach described herein (as well as using nanoparticle probes with or as smart probes). Complementing other modalities, FMT of degraded EC glycocalyx of capillaries in low FSS would serve as a generalized yet sensitive inflammatory indicator of early pathogenesis in nearby tissues, which carries a diagnostic advantage over current approaches in development that have a smaller disease spectrum due to disease-specific targets. Other approaches include magnetic nanoparticle probes for MRI imaging, and post-isolation of tissue for regional characterization in animal studies. In some embodiments, characterization can be associated with invasive diagnostics, such as blood collection devices and minimally invasive nanotainers.

Figures 11A, 11B, 11C:
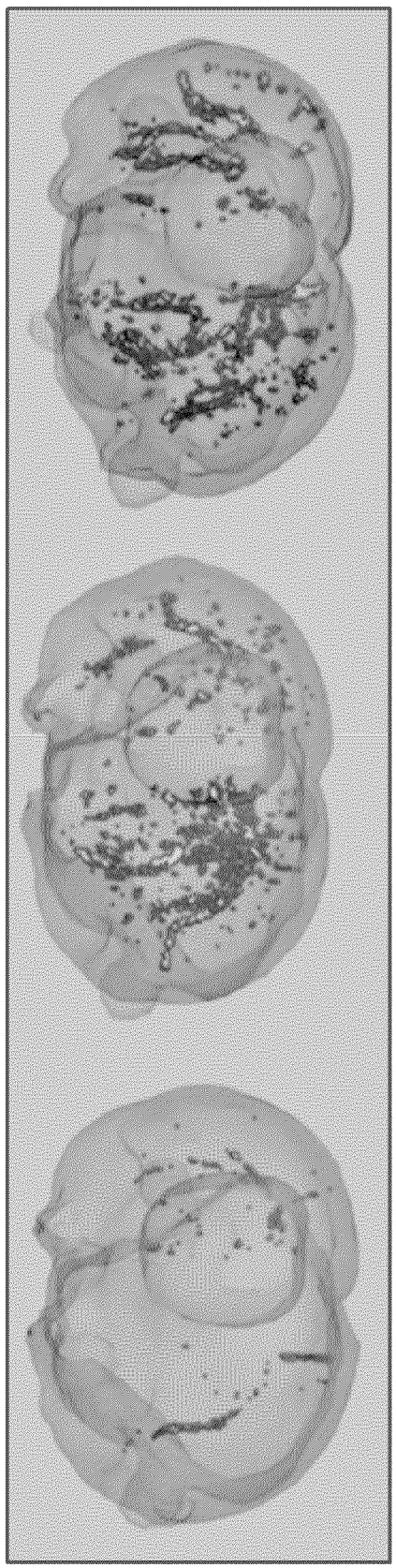
FIGS. 11A, 11B, and 11C show theoretical images obtained using embodiments of the nanoparticle probes disclosed herein.

FIGS. 11A, 11B, and 11C show imaging of a brain that could be achieved using the disclosed nanoparticle probes. Glyconanoparticle distribution in (A) Control, (B) Multiple Sclerosis, and (C) Stroke animals models used for disease detection or diagnosis of neuroinflammation. Glyconanoparticles are functionalized with sialyl-LeX, which is a carbohydrate ligand that has an affinity to E-selectin, which is upregulated during inflammation.

Delivery of Nanoparticles for Therapeutic Effects in Areas of Microcirculatory Dysfunction: FSS/glycocalyx-dependent targeting applied to carriers can enhance the therapeutic delivery of agents, such as siRNA and biologics to microvascular ECs in low FSS conditions characterized by a thin glycocalyx layer. In some embodiments, this targeted region is a pathophysiological site for treatment strategies. Furthermore, in some embodiments, nanoparticle probes have a dimension of at least 15 nm to not undergo capillary diffusion unless in cancer.

Delivery of Mechanosensor Prosthetics to Lower FSS Detection of Mechanoreceptors: The vascular endothelium is an early site of damage during inflammation. Thus, lowering FSS threshold detection would preserve the endothelial surface layer of microcirculatory vessels under microvascular dysfunction and would reduce damage caused by either chronic low-grade inflammation or reperfusion. Adverse effects on physiological processes can be limited or avoided if the nanoparticle probe design (tether dimensions, possibly <100 nm length and <15 nm diameter) limits its binding to cells below a specified glycocalyx thickness of interest.

In some embodiments, the nanoparticle probes described herein, having FSS/glycocalyx-thickness-dependent cell surface targeting, would not only expand vascularization strategies in tissue engineering, but also could be used to develop an alternative mechanism to enhance the effectiveness of cell-based therapeutics.

In theranostic applications, a generalized yet sensitive region-specific inflammatory/viscous composite biomarker such as those described herein would lead to further advances in the field of screening and early detection of various chronic conditions, when treatments are more viable. Furthermore, in some instances, identifying regions with early inflammatory damage in the microcirculation is more advantageous for investigating integrative medicine, where regions with subtle improvements can be identified for high-throughput analysis and where alternative non-invasive diagnostic approaches can be improved, such as proteomics or metabolomics of skin surface collections. In some embodiments, the nanoparticle probes are used to facilitate the investigation of pathways involved in the high remission rate (with rare cases of relapse) of various chronic diseases despite poor prognosis, induced by a non-traumatic region-specific pulsatile blunt force targeting observed in a private practice.

From potentially addressing the source rather than the symptom of various chronic conditions, the mechanotransduction-based therapy, in some embodiments, is likely mediated through deformation of the extracellular matrix (ECM) that leads to downstream synergistic biological responses, such as stem cell activation and/or viscous alterations in hemodynamics or interstitial fluid dynamics. In some embodiments, the following uses of nanoparticle probes are possible: (1) simulating this biological phenomenon by altering cellular response to the surrounding FSS and by targeting ECs characterized by a degraded glycocalyx in pathophysiology, (2) creating a novel translational tool to explore this new field, and (3) accounting for the potential role(s) of the primo vascular system involved in stem cell transport and investigating epigenetic mechanisms.

To reduce FSS threshold of CD29 in ECs with a thin glycocalyx, an anti-CD29 nanobody (sdAb) or single chain variable fragment (scFv) functionalized DNA-origami prosthetic is designed. Taking advantage of the negative charge of DNA, sterical hindrance, and tether length of the nanobody (<100 nm), the designed prosthetic has a higher affinity to targeted receptors of ECs characterized by a glycocalyx below a specified thickness. The parameters of the prosthetic will be determined based on pilot studies on its functions, such as eliciting an appropriate drag force in low FSS conditions. The construct will incorporate a functionalized dendrimer base or other structural base that utilizes a low-affinity slip bond, against EC glycocalyx surface determinants. This feature would increase the carrier's affinity to the glycocalyx if necessary and would not interfere with the nanoparticle probe's mechanical mechanism for CD29 stimulation, since the secondary target would not restrict CD29 activation in response to FSS-induced hydrodynamic drag. With the base, in high FSS conditions, the increase in cell membrane fluidity lowers binding time, in contrast to low FSS conditions. The primary objective of this application is to improve current vascularization techniques in tissue engineering. Additional designs and applications depend on the desired goal of the project.

Therapeutic strategies and other methodologies targeting the glycocalyx with non-specific alterations (which include stem cell coatings and proteoglycan mimetics) are unable to achieve the specific purpose of this proposed application. This is due to the presence of an intact glycocalyx, which prevents accessibility to the site of interest. Furthermore, a degraded glycocalyx, with deglycanated fibronectin bounded to CD29, or a very thick glycocalyx would reduce the sensitivity of the mechanosensor, which necessitates a more targeted approach. Furthermore, there is no simple pharmaceutical drug to achieve FSS-induced responses due to the physical activating mechanism behind mechanoreceptors. Manipulation via magnetic nanoparticle probes and composite scaffolds can achieve these responses; however, these methods have a potential issue with biocompatibility and toxicity that would need to be addressed in the future, and are FSS-independent methods.

In some embodiments, project feasibility is dependent on known dimensions and properties of cells in the microcirculation to determine the parameters most useful to develop the proposed technology. In the glycocalyx of ECs, the spacing between glycans (GAGs) can be about 20 nm, and is assumed to be ubiquitous. Glycocalyx thickness in diseased EC capillaries range from 10 nm to 30 nm in comparison to the control range of 60 nm to 80 nm, but these measurements are region-dependent. CD29 on the EC apical surface mediates FSS signaling, and the extracellular domain of CD29 has a height of 1 nm, which is about the span of selectins and other integrin receptors. Based on mAb-magnetic bead studies, CD29 activation occurs with 1.2 pN pulling force in cardiomyocytes and 200 pN in MSCs. In some embodiments, a threshold below 1.2 pN in ECs can be used since EC glycocalyx thickness is close to cardiomyocytes and should have similar mechanoreceptor properties. In some embodiments, a force of 130 pN, which is equivalent to ~10% of drag force experienced by a 30 μm×30 μm EC with FSS of 12 dynes/cm², results in integrin mechanosensory complex activation. Thus, in some embodiments, the EC CD29 threshold would need to be verified for refining modeling parameters. Laminar flow is essential, since twisting CD29 in ECs, which simulates turbulent flow, will result in a different signal transduction. In some embodiments, the average superficial flow velocity of bone grafts in bioreactors is about 0.06 cm/s, ranging from 0.0001 to 0.15 cm/s in different regions. In some embodiments, the nanoparticle probes have a dimension of at least 15 nm to not undergo capillary diffusion unless in cancer.

In some embodiments, the dimension of an Fab fragment of an IgG antibody (nanobody) is about 8 nm×4 nm×5 nm. In some embodiments, the rationale for the general size of the nanoparticle probe can be is as follows: for a Peclet number (convection:diffusion)=1, in a small capillary (~3 μm), in order for convection to partially dominate in the lower limits of fluid flow in the bioreactor (~1-10 μm/sec), the nanoparticle probe can have a diameter ranging from ~20-160 nm.

In some embodiments, a model to estimate the drag force on the DNA origami can be used. Previous attempts to model hydrodynamic drag on tethered DNA strands using statistical mechanics have been verified experimentally by holding one end of the DNA with optical tweezers and exposing the other end to hydrodynamic flow. However, DNA origami bundles have increased stiffness therefore making bending contributions negligible. Moreover, in some embodiments, it would be more accurate to model the entire DNA origami but not accurate to consider the effect of hydrodynamic drag on a known material with approximately the same geometry, such as a solid cone.

In some embodiments, hydrodynamic drag force is often modeled using Stoke's drag force expression: $F_d = 6\pi C_{shape} C_{tether} \eta r v$, where $\eta$ is the coefficient of viscosity, r the radius of the particle (radius of cone), and v the velocity of the fluid (assuming the tethered particle has no velocity). $C_{shape}$ and $C_{tether}$ are correction coefficients for the shape of the DNA origami and the fixed end, as Stoke's drag force expression originally assumes spherical particles in free flow. In some embodiments, an empirical expression of $C_{shape}$ (also known as the dynamic shape factor) for axisymmetric shapes, such as a cone, with motion normal to the axis of symmetry: $C_{shape} = 0.392 + 0.621 S - 0.040 S2$, where S is the ratio of the surface area of the cone, divided by the surface area of a sphere that has the same perimeter as the side perimeter of the cone. In some embodiments, a tethering correction coefficient developed can be used:

$$C_{tether} = \sum_{i=0}^{N} c_i h^{-i}$$

where h is the ratio of the cone radius and length, and $c_i$ are fitted coefficients.

However, in some embodiments, this is much larger than the actual force on tethered DNA origami.

In some embodiments, antibody detachment threshold is unlikely to occur in using the following parameters. In some embodiments, 250 pN on an anti-CD29 mAb results in 0% antibody detachment, and 350 pN results in 15% detachment. In some embodiments, the epitope of interest or selected mAb is selected so that it does not interfere with CD29 function, since attachment at functional sites such as hinge regions could prevent CD29 activation. Other mAb types include activating CD29 mAbs that target activated CD29 and prevent its deactivation, and for clarification, cannot bind to non-active CD29. Thus, in some embodiments, an anti-CD29 mAb can be selected to avoid these potential issues.

Engineering of sdAbs are commercially available by Creative-Biolabs, and oriented conjugation of sdAbs to nanoparticle probes are feasible as an alternate application via C-terminus attachment of 6-His-Cys by mutagenesis. Specific attachment of oligonucleotides to the C-terminus of sdAbs or other proteins can be achieved. Functionalization of DNA origami structures with this product and protocols for increased yield after purification can be done using synthetic techniques. In some embodiments, DNA origami design/modeling of 3D nanostructures and their synthesis can follow standardized protocols, and commercial services are also available through Tilibit Nanosystems. Base rupture is unlikely (dG/dC ~20 pN; dA/dT ~14 pN; stacking 2 pN). Lyosomal degradation of DNA nanodevices following apical CD29 internalization or recycling in ECs, if it occurs, would pose no problem for the immune system following transplantation, unless antigen presenting ECs are capable of presenting the degraded product as an antigen detectable by DNA receptors; however, this can be addressed with nucleases. Inactivation, removal, or absence of nuclease in media typically present in serum would ensure in vitro stability of the DNA nanodevice, and this non-permanent feature can be used to ensure degradation of DNA-exposed products prior to transplantation. Much progress have been made in translating this technology to the cell. Recent progress have been made for DNA origami stability in serum.

Although dendrimer synthesis is well-established, in some embodiments a low affinity ligand, sialyl Lex, has 50 pN binding strength to selectin sites with a fast off-on rate that varies by force and ramp rate. In some embodiments, finding a weak or weaker low-affinity ligand or analog to glycocalyx targets is a potential concern. However, in some embodiments, an alternative solution is using weak-affinity antibodies, whose isolation will be feasible with commercial purification kits used for conducting affinity chromatography. In some embodiments, the degree in which membrane fluidity affects the time for CD29 to bind via dragging of the slip bond is unknown and its effect on nanoparticle probe function can be validated. In some embodiments, synergistic signaling among mechanosensors in response to FSS will not be accounted for in order to reduce the complexity of the research design. Determining if low flow regions in bioreactors have sufficient nutrients can be investigated, in addition to monitoring the surrounding cell density. In some embodiments, stabilizing mature vessels in lower FSS regions and stimulating sprouting in near-static regions in a 3D perfusion bioreactor may make use of additional approaches, such as alterations in media, to utilize the phenotypic change to develop a robust prevascularized construct.

In some embodiments, nanoparticle probe size/shape can be determined using: optical tweezers near a surface and nanoparticle tracking analysis. In some embodiments, the velocity conditions at which brownian force outweighs the drag force to drive the designed nanoparticle probe near a vessel wall can also be investigated. These parameters can be based on variations of the rudimentary prosthetic design (FIG. 7), in order to determine the ideal dimensions prior to conducting future studies.

In some embodiments, potential targets include vascularized tissue engineering. Vascularized bone tissue engineering generally utilize a co-culture of MSCs and EPCs, and it is assumed that stem cells express a thick glycocalyx and reside in a low FSS niche. Whether differentiated cell types, such as osteocytes and pericytes, exhibit a thinning of the glycocalyx in low FSS conditions is yet unknown. Although this is a potential concern, it is interesting to note that preliminary studies, suggest that shear stress induces vasoprotective gene upregulation in pericytes. Furthermore, osteocytes regulates bone reformation in response to FSS-induced CD29, and would be either beneficial or have little effect on the project's application. If MSCs are targeted, though unlikely due to their probable glycocalyx thickness, similar CD29-induced FSS responses and ECM interactions and responses would apply.

Targeting of cell types other than ECs could occur and, in some embodiments, exploited. In some instances, stem cells express a thick glycocalyx and reside in a low FSS niche. Increased FSS induces proliferation and differentiation in adult stem cells, but induces proliferation for most differentiated cells. In some embodiments, differentiated cell types, such as pericytes and osteocytes, exhibit a thinning of the glycocalyx in low FSS conditions or have a limited glycocalyx thickness range and can be targeted. Shear stress could induce vasoprotective gene upregulation in pericytes. Furthermore, FSS controls bone remodeling in osteocytes. Modifications can include attachment of bioactive molecules (enzymes, ligands, etc) and/or functional nanobodies (quantum dots, magnetic nanoparticles, DNA and/or RNA origami, niosomes, liposomes, polymeric nanoparticles, etc) for various applications. Thus based on available knowledge on glycocalyx thicknesses, in some embodiments, biomedical applications for microvascular endothelial cells are feasible. In some embodiments, targeting can be done for any of these cell types but is not limited to these cell types.

Figure 7A:
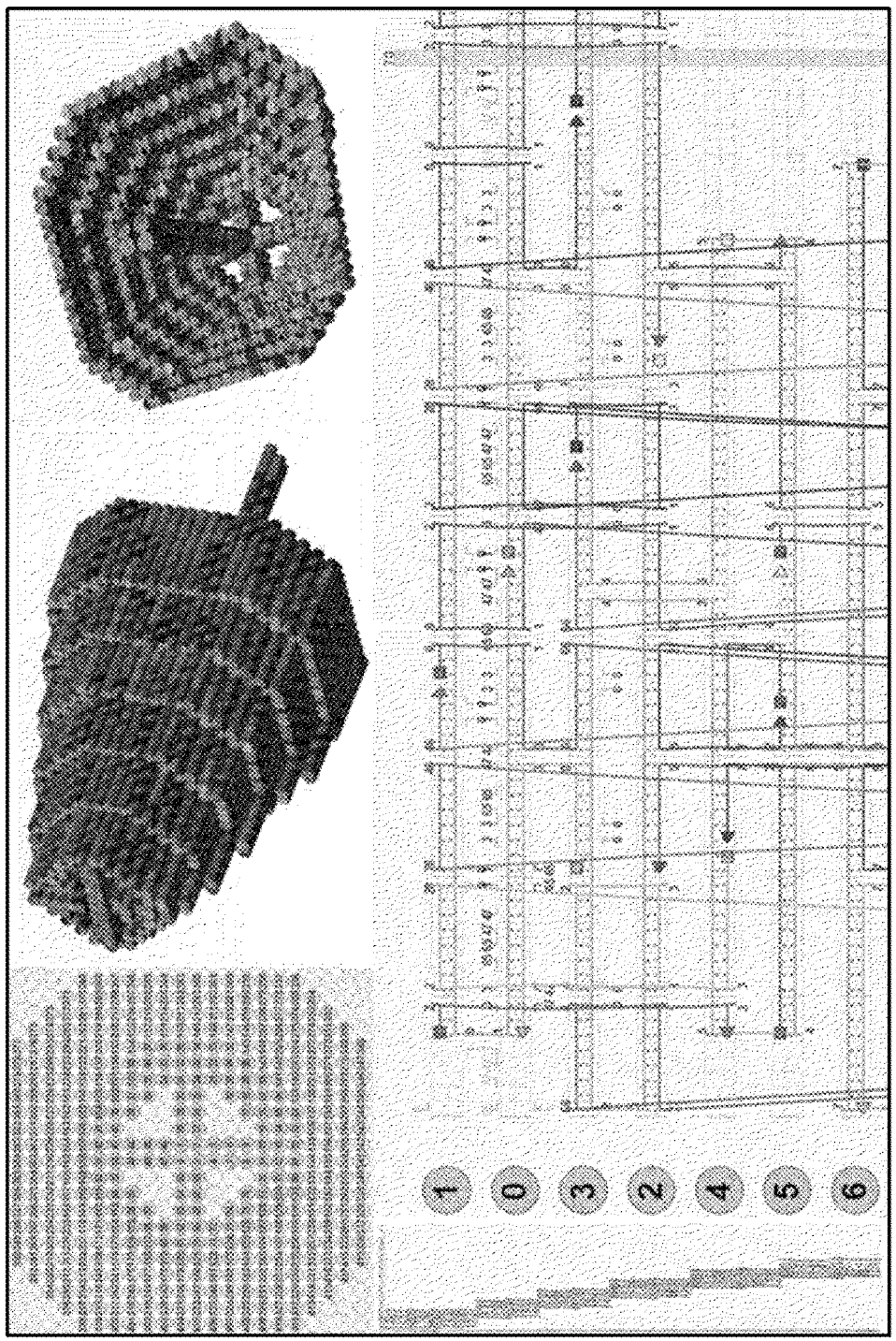
FIG. 7A shows a design for DNA origami (prosthetic) with sequence and crossovers.
Figure 7B:
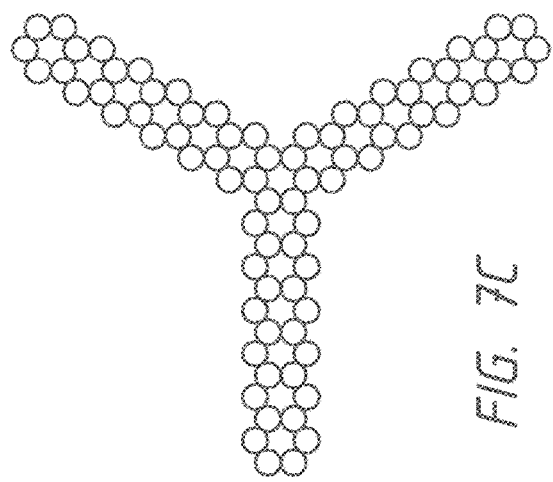
FIGS. 7B-7F show embodiments of possible DNA origami constructs.
Figure 7C:
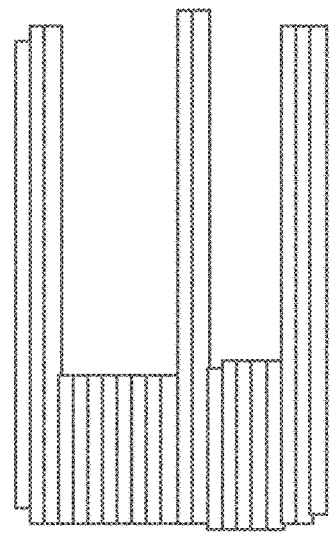
Figure 7D:
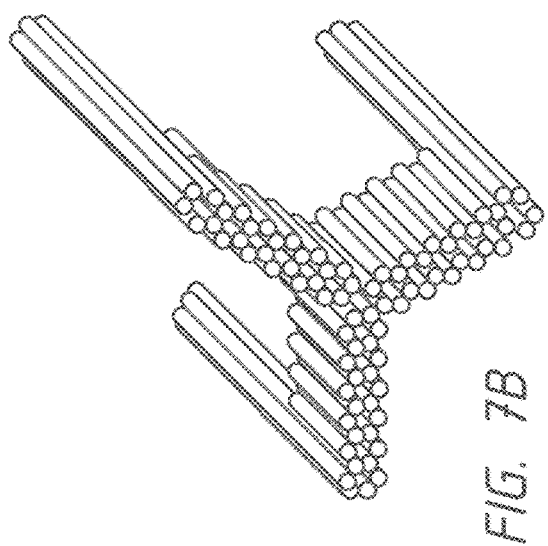
Figure 7E:
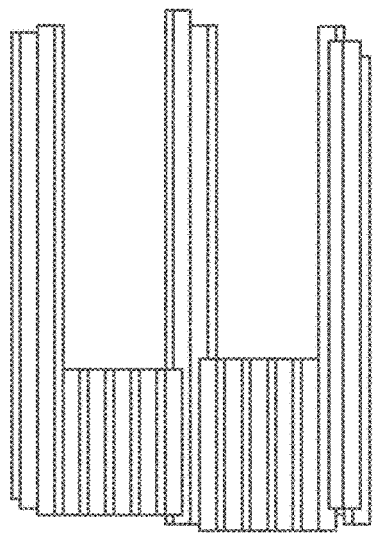
Figure 7F:
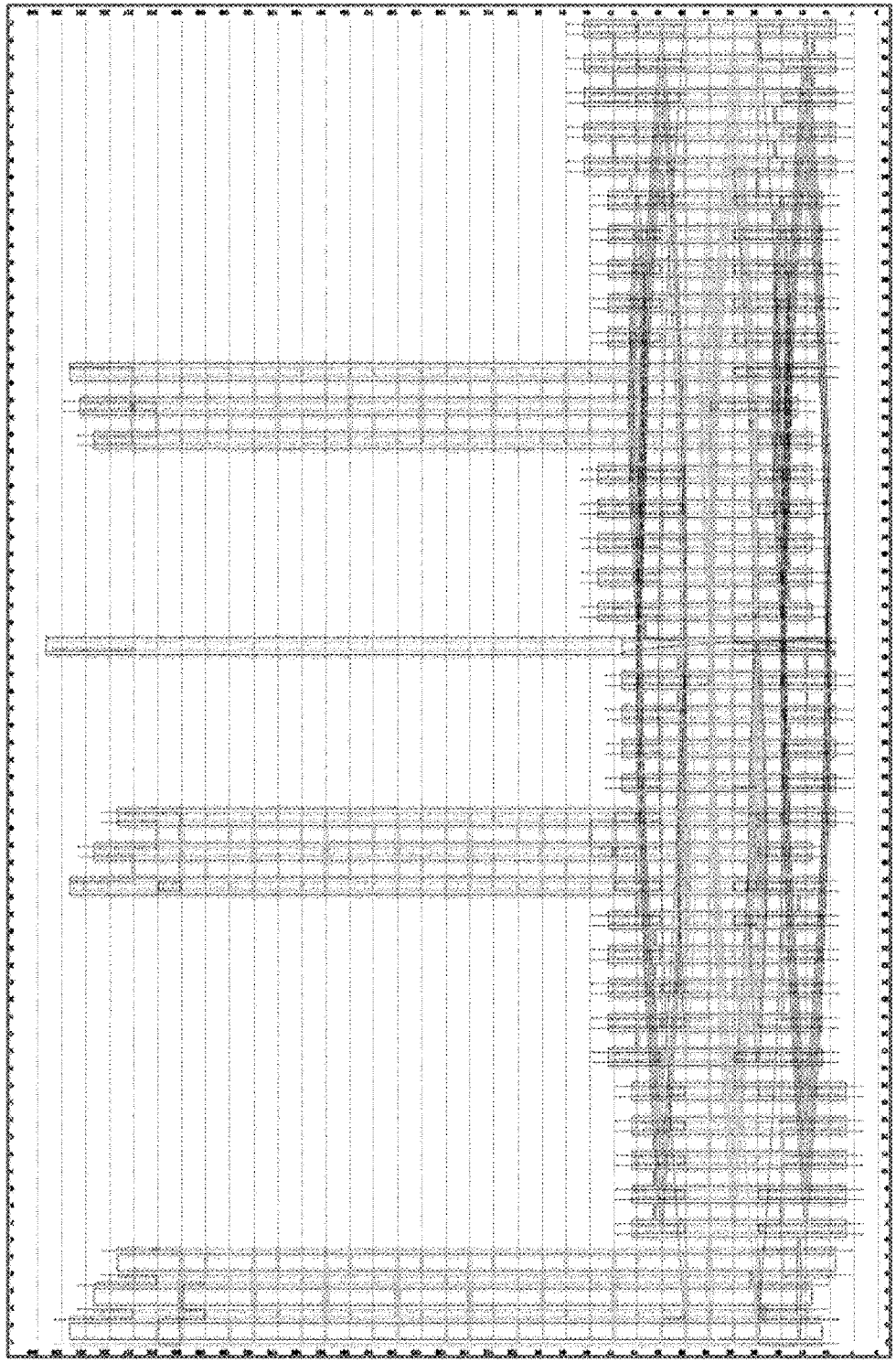
Figure 8B:
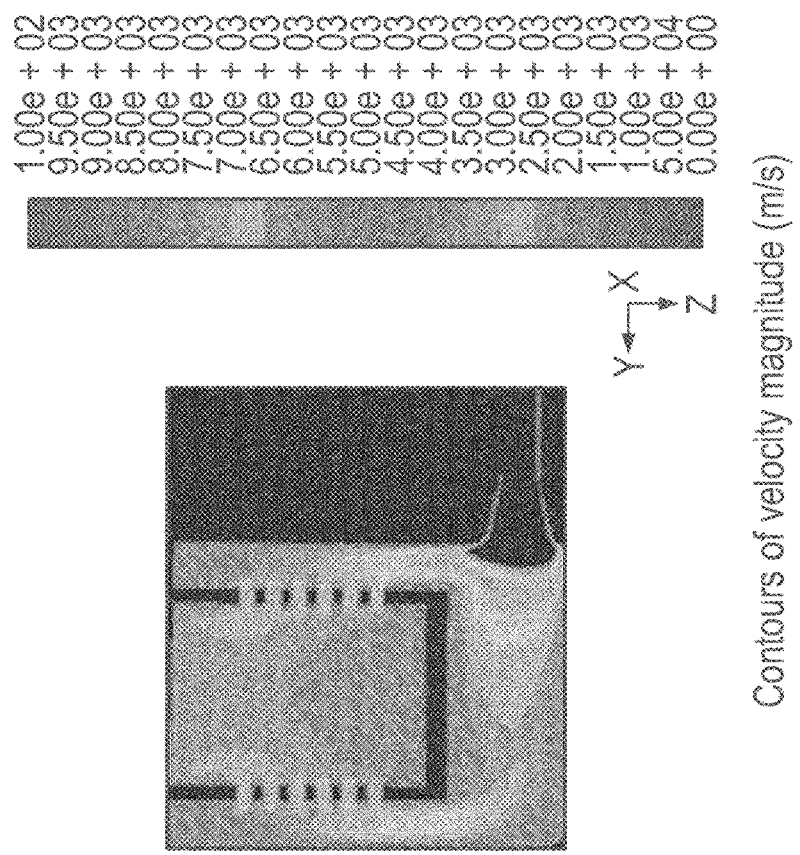
FIGS. 8A and 8B show flow diagrams of bioreactors.
Figure 8A:
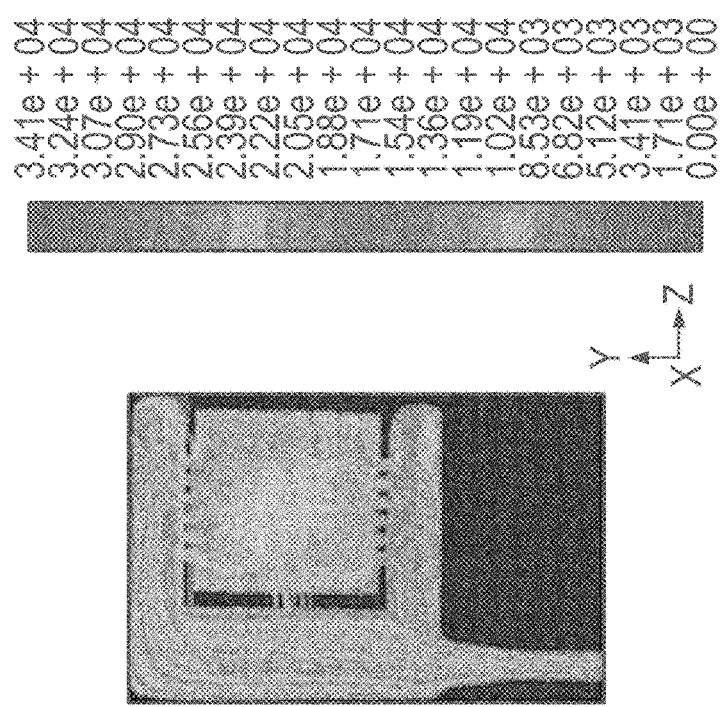

FIG. 7A shows a design for DNA origami (prosthetic) with sequence and crossovers. Sequence design of scaffold and synthesis of staple strands can be based off known methods. The proposed design is comprised of a 24,210 base scaffold with 730 staple strands, and has the approximate dimensions: cylindrical core length (314 bp, ~100 nm), cone length (220 bp, ~75 nm), diameter (44-50 nm), inner diameter (~26 nm). The hollow structure permits extracellular debris (>6 nm) to coalesce with higher frequency after tethering to a target, but depends upon the electrostatic attraction between the DNA and debris. This increases the potential hydrodynamic drag of the prosthetic in low FSS conditions.

FIGS. 7B-7F show models of DNA origami to target epitopes hidden by the EC glycocalyx. The DNA origami construct is linked to a fluorescent oligonucleotide-QD from Gene Link, connected via single flexible tether at the linkage site labeled in red. A VHH anti-ICAM1 antibody biotinylated at the C-terminus is purchased from Creative Biolabs. ICAM1 was selected as a target due to commercial availability. The experimental design has the antibody conjugated to the tip of each of the 3 tethers. For the control design, the antibody is above the body of the structure, opposing the tethers. Despite the negative charge of DNA origami, penetration may not be an issue, since a 15 nm×100 nm, 24 double helix bundle DNA origami rod, singly penetrates the glycocalyx of HUVECs in static conditions in contrast to its single helix control design. In some embodiments, the protrusions and/or tethers penetrate the glycocalyx more easily than the body of the structure. In some embodiments, this modification improves the limit of detection for inflammation by vascular-targeting nanoparticles. The nucleotide sequence of the FIG. 7F construct is as follows SEQ ID: 1:

```
   1 aatgctacta ctattagtag aattgatgcc acctttttcag ctcgcgcccc aaatgaaaat
  61 atagctaaac aggttattga ccatttgcga aatgtatcta atggtcaaac taaatctact
 121 cgttcgcaga attgggaatc aactgttaca tggaatgaaa cttccagaca ccgtacttta
 181 gttgcatatt taaaacatgt tgagctacag caccagattc agcaattaag ctctaagcca
 241 tccgcaaaaa tgacctctta tcaaaaggag caattaaagg tactctctaa tcctgacctg
 301 ttggagtttg cttccggtct ggttcgcttt gaagctcgaa ttaaaacgcg atatttgaag
 361 tctttcgggc ttcctcttaa tcttttttgat gcaatccgct ttgcttctga ctataatagt
 421 cagggtaaag acctgatttt tgatttatgg tcattctcgt tttctgaact gtttaaagca
 481 tttgagggg attcaatgaa tatttatgac gattccgcag tattggacgc tatccagtct
 541 aaacatttta ctattacccc ctctggcaaa acttcttttg caaaagcctc tcgctatttt
 601 ggttttatc gtcgtctggt aaacgagggt tatgatagtt ttgctcttac tatgcctcgt
 661 aattcctttt ggcgttatgt atctgcatta gttgaatgtg gtattcctaa atctcaactg
 721 atgaatcttt ctacctgtaa taatgttgtt ccgttagttc gttttattaa cgtagatttt
 781 tcttcccaac gtcctgactg gtataatgag ccagttctta aaatcgcata aggtaattca
 841 caatgattaa agttgaaatt aaaccatctc aagcccaatt tactactcgt tctggtgttc
 901 tcgtcagggc aagccttatt cactgaatga gcagctttgt tacgttgatt tgggtaatga
 961 atatccggtt cttgtcaaga ttactcttga tgaaggtcag ccagcctatg cgcctggtct
1021 gtacaccgtt catctgtcct ctttcaaagt tggtcagttc ggttccctta tgattgaccg
1081 tctgcgcctc gttccggcta agtaacatgg agcaggtcgc ggatttcgac acaatttatc
1141 aggcgatgat acaaatctcc gttgtacttt gtttcgcgct tggtataatc gctggggggtc
1201 aaagatgagt gttttagtgt attctttcgc ctctttcgtt ttaggttggt gccttcgtag
1261 tggcattacg tattttaccc gtttaatgga aacttcctca tgaaaaagtc tttagtcctc
1321 aaagcctctg tagccgttgc taccctcgtt ccgatgctgt cttttcgctgc tgagggtgac
1381 gatcccgcaa aagcggcctt taactccctg caagcctcag cgaccgaata tatcggttat
1441 gcgtgggcga tggttgttgt cattgtcggc gcaactatcg gtatcaagct gtttaagaaa
1501 ttcacctcga aagcaagctg ataaaccgat acaattaaag gctccttttg gagcctttttt
1561 ttttggagat tttcaacgtg aaaaaattat tattcgcaat tcctttagtt gttcctttct
1621 attctcactc cgctgaaact gttgaaagtt gtttagcaaa accccataca gaaaattcat
1681 ttactaacgt ctggaaagac gacaaaactt tagatcgtta cgctaactat gagggttgtc
1741 tgtggaatgc tacaggcgtt gtagtttgta ctggtgacga aactcagtgt tacggtacat
1801 gggttcctat tgggcttgct atccctgaaa atgagggtgg tggctctgag ggtggcggtt
1861 ctgagggtgg cggttctgag ggtggcggta ctaaacctcc tgagtacggt gatacaccta
1921 ttccgggcta tacttatatc aaccctctcg acggcactta tccgcctggt actgagcaaa
1981 accccgctaa tcctaatcct tctcttgagg agtctcagcc tcttaatact ttcatgtttc
2041 agaataatag gttccgaaat aggcaggggg cattaactgt ttatacgggc actgttactc
2101 aaggcactga ccccgttaaa acttattacc agtacactcc tgtatcatca aaagccatgt
2161 atgacgctta ctggaacggt aaattcagag actgcgcttt ccattctggc tttaatgaag
2221 atccattcgt ttgtgaatat caaggccaat cgtctgacct gcctcaacct cctgtcaatg
2281 ctggcggcgg ctctggtggt ggttctggtg gcggctctga gggtggtggc tctgagggtg
2341 gcggttctga gggtggcggc tctgaggag gcggttccgg tggtggctct ggttccggtg
2401 attttgatta tgaaaagatg gcaaacgcta ataagggggc tatgaccgaa aatgccgatg
```

-continued

```
2461 aaaacgcgct acagtctgac gctaaaggca aacttgattc tgtcgctact gattacggtg 2521 ctgctatcga tggtttcatt ggtgacgttt ccggccttgc taatggtaat ggtgctactg 2581 gtgattttgc tggctctaat tcccaaatgg ctcaagtcgg tgacggtgat aattcacctt 2641 taatgaataa tttccgtcaa tatttacctt ccctccctca atcggttgaa tgtcgccctt 2701 ttgtctttag cgctggtaaa ccatatgaat tttctattga ttgtgacaaa ataaacttat 2761 tccgtggtgt ctttgcgttt cttttatatg ttgccacctt tatgtatgta ttttctacgt 2821 ttgctaacat actgcgtaat aaggagtctt aatcatgcca gttcttttgg gtattccgtt 2881 attattgcgt ttcctcggtt tccttctggt aactttgttc ggctatctgc ttacttttct 2941 taaaaagggc ttcggtaaga tagctattgc tatttcattg tttcttgctc ttattattgg 3001 gcttaactca attcttgtgg gttatctctc tgatattagc gctcaattac cctctgactt 3061 tgttcagggt gttcagttaa ttctcccgtc taatgcgctt ccctgttttt atgttattct 3121 ctctgtaaag gctgctattt tcattttga cgttaaacaa aaaatcgttt cttatttgga 3181 ttgggataaa taatatggct gtttattttg taactggcaa attaggctct ggaaagacgc 3241 tcgttagcgt tggtaagatt caggataaaa ttgtagctgg gtgcaaaata gcaactaatc 3301 ttgatttaag gcttcaaaac ctcccgcaag tcgggaggtt cgctaaaacg cctcgcgttc 3361 ttagaatacc ggataagcct tctatatctg atttgcttgc tattgggcgc ggtaatgatt 3421 cctacgatga aaataaaaac ggcttgcttg ttctcgatga gtgcggtact tggtttaata 3481 cccgttcttg gaatgataag gaaagacagc cgattattga ttggtttcta catgctcgta 3541 aattaggatg ggatattatt tttcttgttc aggacttatc tattgttgat aaacaggcgc 3601 gttctgcatt agctgaacat gttgtttatt gtcgtcgtct ggacagaatt actttacctt 3661 ttgtcggtac tttatattct cttattactg gctcgaaaat gcctctgcct aaattacatg 3721 ttggcgttgt aaatatggc gattctcaat taagccctac tgttgagcgt tggctttata 3781 ctggtaagaa tttgtataac gcatatgata ctaaacaggc ttttttctagt aattatgatt 3841 ccggtgttta ttcttatttta acgccttatt tatcacacgg tcggtatttc aaaccattaa 3901 atttaggtca gaagatgaaa ttaactaaaa tatatttgaa aaagttttct cgcgttcttt 3961 gtcttgcgat tggatttgca tcagcattta catatagtta tataacccaa cctaagccgg 4021 aggttaaaaa ggtagtctct cagacctatg attttgataa attcactatt gactcttctc 4081 agcgtcttaa tctaagctat cgctatgttt tcaaggattc taagggaaaa ttaattaata 4141 gcgacgattt acagaagcaa ggttattcac tcacatatat tgatttatgt actgtttcca 4201 ttaaaaaagg taattcaaat gaaattgtta aatgtaatta attttgtttt cttgatgttt 4261 gtttcatcat cttcttttgc tcaggtaatt gaaatgaata attcgcctct gcgcgatttt 4321 gtaacttggt attcaaagca atcaggcgaa tccgttattg tttctcccga tgtaaaaggt 4381 actgttactg tatattcatc tgacgttaaa cctgaaaatc tacgcaattt ctttatttct 4441 gtttacgtg ctaataattt tgatatggtt ggttcaattc cttccataat tcagaagtat 4501 aatccaaaca atcaggatta tattgatgaa ttgccatcat ctgataatca ggaatatgat 4561 gataattccg ctccttctgg tggtttcttt gttccgcaaa atgataatgt tactcaaact 4621 tttaaaatta ataacgttcg ggcaaaggat ttaatacgag ttgtcgaatt gtttgtaaag 4681 tctaatactt ctaaatcctc aaatgtatta tctattgacg gctctaatct attagttgtt 4741 agtgcaccta agatattttt agataacctt cctcaattcc tttctactgt tgatttgcca 4801 actgaccaga tattgattga gggtttgata tttgaggttc agcaaggtga tgctttagat 4861 ttttcatttg ctgctggctc tcagcgtggc actgttgcag gcggtgttaa tactgaccgc
```

```
4921 ctcacctctg ttttatcttc tgctggtggt tcgttcggta tttttaatgg cgatgtttta
4981 gggctatcag ttcgcgcatt aaagactaat agccattcaa aaatattgtc tgtgccacgt
5041 attcttacgc tttcaggtca gaagggttct atctctgttg ccagaatgt ccctttatt
5101 actggtcgtg tgactggtga atctgccaat gtaaataatc catttcagac gattgagcgt
5161 caaaatgtag gtatttccat gagcgttttt cctgttgcaa tggctggcgg taatattgtt
5221 ctggatatta ccagcaaggc cgatagtttg agttcttcta ctcaggcaag tgatgttatt
5281 actaatcaaa gaagtattgc tacaacggtt aatttgcgtg atggacagac tcttttactc
5341 ggtggcctca ctgattataa aaacacttct caagattctg gcgtaccgtt cctgtctaaa
5401 atccctttaa tcggcctcct gtttagctcc cgctctgatt ccaacgagga aagcacgtta
5461 tacgtgctcg tcaaagcaac catagtacgc gccctgtagc ggcgcattaa gcgcggcggg
5521 tgtggtggtt acgcgcagcg tgaccgctac acttgccagc gccctagcgc ccgctccttt
5581 cgctttcttc ccttcctttc tcgccacgtt cgccggcttt ccccgtcaag ctctaaatcg
5641 ggggctccct ttagggttcc gatttagtgc tttacggcac ctcgacccca aaaaacttga
5701 tttgggtgat ggttcacgta gtgggccatc gccctgatag acggttttc gccctttgac
5761 gttggagtcc acgttcttta atagtggact cttgttccaa actggaacaa cactcaaccc
5821 tatctcgggc tattcttttg atttataagg gattttgccg atttcggaac caccatcaaa
5881 caggattttc gcctgctggg gcaaaccagc gtggaccgct tgctgcaact ctctcagggc
5941 caggcggtga agggcaatca gctgttgccc gtctcgctgg tgaaaagaaa aaccaccctg
6001 gcgcccaata cgcaaaccgc ctctccccgc gcgttggccg attcattaat gcagctggca
6061 cgacaggttt cccgactgga aagcgggcag tgagcgcaac gcaattaatg tgagttagct
6121 cactcattag gcaccccagg ctttacactt tatgcttccg gctcgtatgt tgtgtggaat
6181 tgtgagcgga taacaatttc acacaggaaa cagctatgac catgattacg aattcgagct
6241 cggtacccgg ggatcctcta gagtcgacct gcaggcatgc aagcttggca ctggccgtcg
6301 ttttacaacg tcgtgactgg gaaaaccctg gcgttaccca acttaatcgc cttgcagcac
6361 atccccttt cgccagctgg cgtaatagcg aagaggcccg caccgatcgc ccttcccaac
6421 agttgcgcag cctgaatggc gaatggcgct ttgcctggtt tccggcacca gaagcggtgc
6481 cggaaagctg gctggagtgc gatcttcctg aggccgatac ggtcgtcgtc ccctcaaact
6541 ggcagatgca cggttacgat gcgcccatct acaccaacgt aacctatccc attacggtca
6601 atccgccgtt tgttcccacg gagaatccga cgggttgtta ctcgctcaca tttaatgttg
6661 atgaaagctg gctacaggaa ggccagacgc gaattatttt tgatggcgtt cctattggtt
6721 aaaaaatgag ctgatttaac aaaaatttaa cgcgaatttt aacaaaatat taacgtttac
6781 aatttaaata tttgcttata caatcttcct gtttttgggg cttttctgat tatcaaccgg
6841 ggtacatatg attgacatgc tagttttacg attaccgttc atcgattctc ttgtttgctc
6901 cagactctca ggcaatgacc tgatagcctt tgtagatctc tcaaaaatag ctaccctctc
6961 cggcattaat ttatcagcta gaacggttga atatcatatt gatggtgatt tgactgtctc
7021 cggcctttct cacccttttg aatctttacc tacacattac tcaggcattg catttaaaat
7081 atatgagggt tctaaaaatt tttatccttg cgttgaaata aaggcttctc ccgcaaaagt
7141 attacagggt cataatgttt ttggtacaac cgatttagct ttatgctctg aggctttatt
7201 gcttaatttt gctaattctt tgccttgcct gtatgattta ttggatgtt
```

Delivery of nanoparticle probes can also be used in the delivery of matrix-degradation enzymes to reduce flow variability. In some embodiments, degrading the extracellular matrix (ECM) can eliminate low FSS regions through decreased internal resistance. In some embodiments, this strategy can be used to enhance endothelialization of a tissue construct in a time-dependent manner. For example, in some embodiments, carriers functionalized with FSS/glycocalyx-dependent technology can be used to release enzymes at low FSS regions. In some embodiments, this release is followed by enzyme deactivation or removal. Removal can be achieved via magnetic field if enzymes are attached to magnetic NPs. In some embodiments, ECM remodeling is essential for activation of stem cell niches, but current limitations in technology prevent direct remodeling of low FSS regions of a scaffold in a bioreactor.

Figure 9:
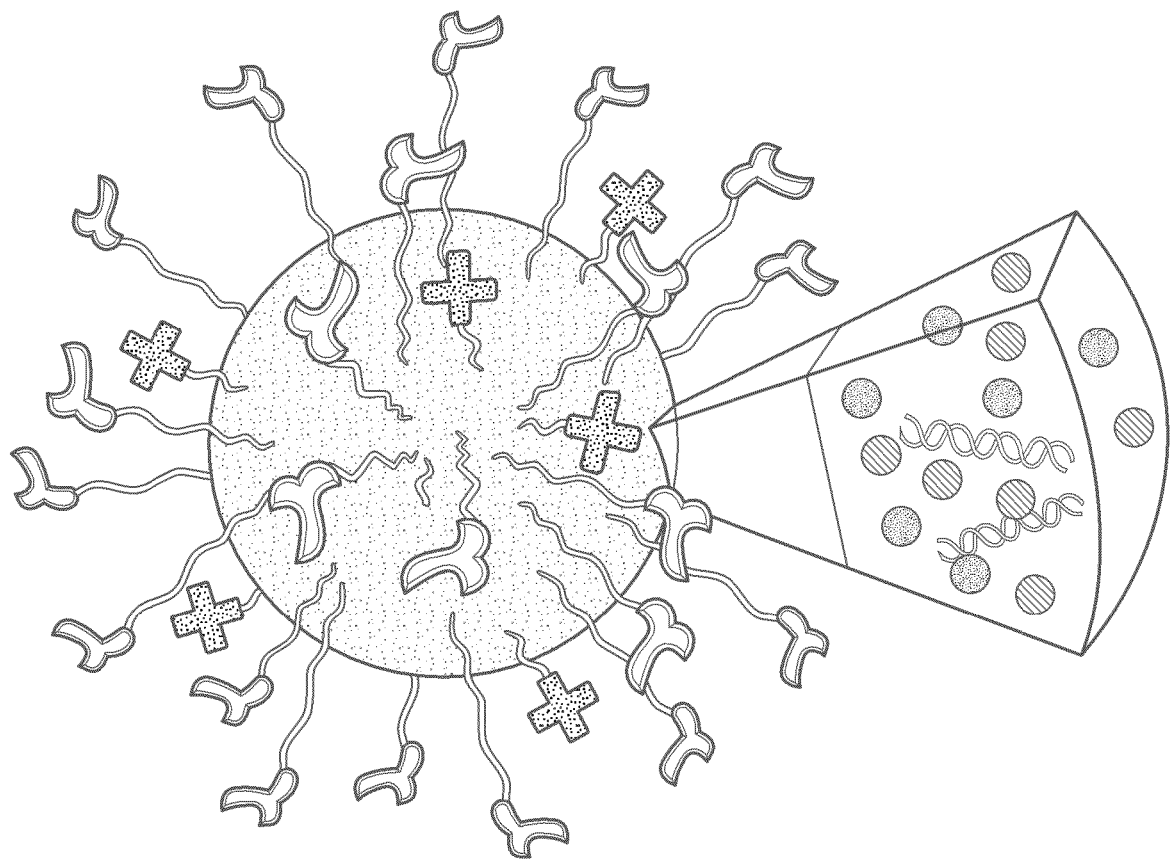
FIG. 9 shows an embodiment of a nanoparticle probe.
Figure 9:
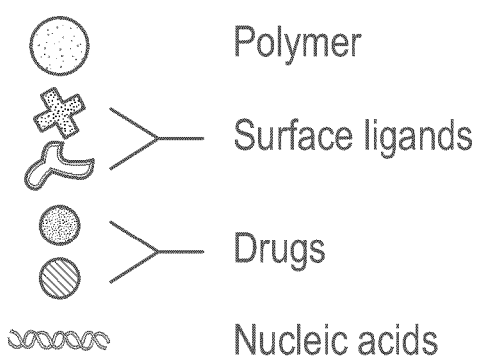

Delivery of nanoparticle probes can also be used to induce local growth factor gradient to enhance endothelialization. In some embodiments, the nanoparticle probes can allow specific targeting of low FSS regions. In some embodiments, this targeting facilitates various strategies in creating a local growth factor gradient, such as the incorporation of the proposed technology to deliver encapsulated VEGF for endothelial sprouting, thereby enhancing vascularization and addressing similar limitations in tissue constructs in low FSS regions. The nanoparticle probes can be functionalized with various active molecules (growth factors, biomolecules, therapeutics, pharmaceuticals, etc.), which can be delivered to a site of interest. FIG. 9 shows a functionalized embodiment of a nanoparticle probe, e.g., a schematic of a functionalized nanoparticle with encapsulated agents (drugs and nucleic acids). Polymeric biodegradation allows control over release kinetics of therapeutic agents. Agents can be functionalized to the surface or inside of the nanoparticle probe, diffused within the nanoparticle probe (hydrophobic or hydrophilic associate), or otherwise associated with the nanoparticle probe. In some embodiments, the nanoparticle nanoprobes can be used to diagnose and treat Type 2 diabetes, hypertension, chronic kidney disease, cancer, etc. by functionalizing an effective therapeutic and a targeting moiety to one of the nanoparticle probes described herein.

Figure 10:
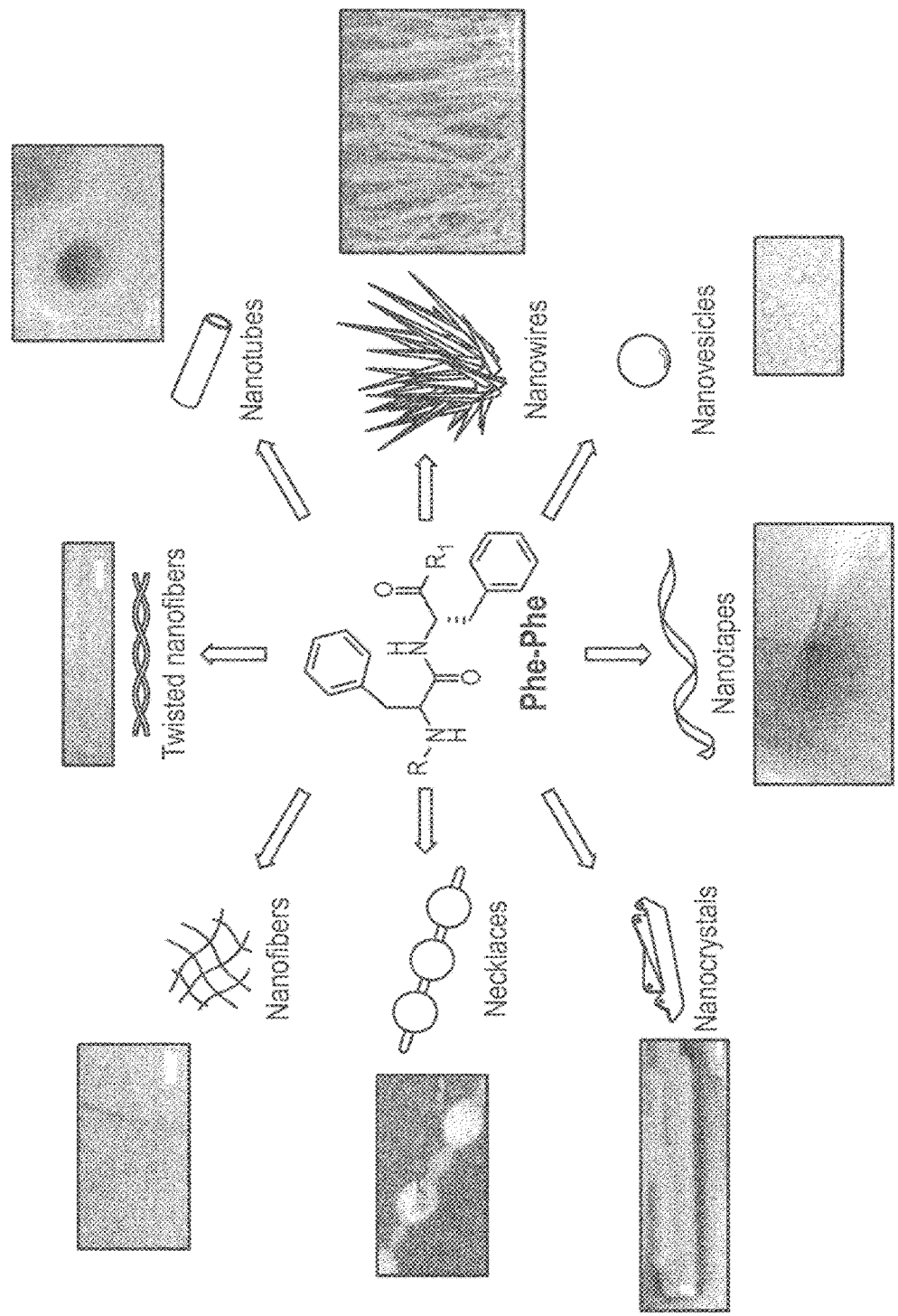
FIG. 10 shows various embodiments, self-assembling structures.

In some embodiments, delivery of self-assembly nanoparticles for bottoms-up modification of tissue scaffolds is accomplished. In some embodiments, this approach can include polymer subunits containing cyclic-RGD motifs (or other motifs) for integrin binding to establish an ECM. The technology for self-assembly of capillary networks in tissue scaffolds are in its early stages. In some embodiments, the delivery of self-assembly nanoparticles at low FSS regions may be used in tissue engineering to establish an initial site (a nucleation site) for self-assembly within a scaffold. Several self-assembling particles are shown in FIG. 10 that could be nucleated using the nanoparticle probes described herein. Examples of self-assembly of compounds bearing Phe-Phe motif for the formation of various structures. In some embodiments, the nanoparticle probes can be applied to various self-assembly subunits, such as peptides. In some embodiments, the nanoparticle probes can be applied to 3D-printed constructs, a bottoms-up tissue engineering approach.

In some embodiments, as discussed elsewhere herein, the nanoparticle probes can be used in in vivo applications. For instance, the association among one or more of low basal chronic inflammation, low FSS, increased viscosity, and glycocalyx degradation in ECs is an important pathophysiological indicator. These include microcirculatory dysfunction in the pathogenesis of various chronic diseases, including diabetes, hypertension, end-stage renal disease, osteoporosis, and other chronic conditions. The development of chronic pathophysiology is an imbalance between the amount of damage and the rate at which the damage is addressed, e.g. removal of insult by leukocytes and repair by adult stem cells and/or pericytes. In addition to mesenchymal stem cells (MSCs), these stem cells include endothelial progenitor cells (EPCs) deriving from the bone marrow that are overall responsible for vascular repair and maintains the integrity of the microcirculation especially through physical exercise. FSS and cytokines interact to control the concentration of E-selectin surface expression in ECs. Damage to endothelium is associated with an increase in circulating ECs from EC denudation or with glycocalyx shedding due to very high FSS or other insults. Endothelial damage is also associated with a degraded EC glycocalyx in low FSS regions from inflammation that results in increased intravascular adhesion by leukocytes and platelets. However, the glycocalyx maintained in postcapillary EC venules are even thicker in low FSS and inflammation. The ability to visualize or target capillary regions with early indications of poor microcirculatory status, would be useful as a theranostic tool in a variety of chronic disease animal models. With an affinity for low FSS conditions and thin glycocalyx, it would improve upon the sensitivity of potential vascular preclinical detection methods, such as glyconanoparticles in neuroinflammation.

In some embodiments, methods of synthesizing (e.g., preparing) the nanoparticle probes described herein include a step of acquiring a nanoparticle base structure. In some embodiments, the nanoparticle base structure is functionalized with a slip bond. In some embodiments, the nanoparticle is functionalized with a tether. In some embodiments, the tether is functionalized to a slip bond. In some embodiments, the tether is functionalized to a hinge. In some embodiments, the hinge is functionalized to a slip bond. In some embodiments, the nanoparticle is functionalized with therapeutic agents. In some embodiments, slip bonds may be replaced with non-slip bonds.

In some embodiments, the methods described herein involve identifying a patient (e.g., a subject) in need of treatment. In some embodiments, a patient may comprise any type of mammal (e.g., a mammal such as a human, cow, sheep, horse, cat, dog, goat, rodent, etc.). Once identified as a patient, the nanoparticle probe is administered to the patient for a period of time. In some embodiments, the period of administration comprises a period starting with the diagnosis of a disease state, for a period of more than about 1 day, about 2 days, about 3 days, about a week, about a month, about two months, or until the disease state subsides. In some embodiments, the nanoparticle probe is administered until a time when the disease state is controlled or cured (e.g., the acute symptoms have subsided, symptoms have decreased to a baseline, risk factors death have decreased, etc.), or for a prescribed period of time of less than about 1 week, about 2 weeks, about 3 weeks, about a month, about two months, about 6 months, or about a year.

In some embodiments, dosing and delivery of the combination of the nanoparticle probe can be performed for periods between 1 day to five days, five days to two weeks, two weeks to a month, a month to twelve months. In some embodiments, dosing and delivery of nanoparticle probe can be performed for periods of at least about 1 day, 5 days, 10 days, 20 days, 30 days, 50 days, 100 days, 200 days, 300 days, ranges and values between the aforementioned values and otherwise.

For purposes of summarizing the disclosure, certain aspects, advantages and features of the inventions have been described herein. It is to be understood that not necessarily any or all such advantages are achieved in accordance with any particular embodiment of the inventions disclosed herein. No aspects of this disclosure are essential or indispensable. In many embodiments, the nanoparticle probe system may be configured differently than illustrated in the figures or description herein. For example, various functionalities provided by the illustrated modules can be combined, rearranged, added, or deleted. In some embodiments, additional or different processors or modules may perform some or all of the functionalities described with reference to the example embodiment described and illustrated in the figures. Many implementation variations are possible.

EXAMPLES

Based on the inventor's research experience, the following results are projected using controlled studies.

Example 1

Due to the unavailability of bone marrow microvascular endothelial cells, human dermal microvascular endothelial cells (HDMEC) and media will be purchased from Promocell [C-12210, C-39220, C-39215] as an alternative. The nanoparticle probe's stability in the cell growth media will be validated prior to use, to determine whether countermeasures to stabilize the DNA origami construct or purify the media will be necessary. HDMECs will be flow adapted at 37° C. for 24 hours at 10 dynes/cm$^2$. A microfluidic system, developed at Johns Hopkins University, that controls oxygen tension and shear stress in cultured cells will be used as described. Cells will be divided into two groups: (1) Treatment Group, and (2) Control Group. The control group will utilize either nanoparticle probe without anti-CD29 functionalization or anti-CD29. The nanoparticle probe concentration will be based on results from a pilot study, whose purpose is to validate the design's overall function. Each treatment group will be carried out in five experimental conditions under steady flow over 24 hrs: (1) Static conditions [0.01 dyne/cm2, 5% $O_2$]; (2) Low FSS conditions [0.05-1 dyne/cm$^2$, 5% O2]; (3) Physiological conditions [10 dyne/cm$^2$, 5% O2]; (4) Inflammatory conditions [1 dyne/cm$^2$, 5% $O_2$, with infusion of C-reactive protein or an alternative glycocalyx degradation inducer based on a previous publication; and (5) Ischemic conditions [1 dyne/cm$^2$, 1% $O_2$]. The inflammatory and ischemic conditions at low flow simulates pathophysiological conditions for glycocalyx degradation in the bioreactor environment.

Objective 1: Investigate FSS/Glycocalyx-Thickness-Dependent Targeting in ECs

Time-lapse fluorescence will be used to continuously monitor nanoparticle probes binding to cells. Time points at 4 hr intervals will be recorded as average fluorescence intensity per cell and statistically analyzed by repeated ANOVA. Colocalization of labeled nanoparticle probes and CD29 will be confirmed using fluorescently labeled anti-CD29 mAb [EMD Millipore] targeting a different epitope than the nanoparticle probe CD29 sdAb. Average glycocalyx thickness will be measured by a standardized two-photon laser scanning microscopy method, and compared among the groups by ANOVA, to determine whether glycocalyx-thickness dependent targeting was achieved.

Objective 2: Investigate Lowered FSS Detection Threshold of CD29 in ECs

The biological responses to measure will include endothelial nitric oxide synthase (eNOS) activity and plasminogen activator inhibitor-1 (PAI-1) activity. The eNOS activity assay [Cayman Chemicals] and PAI assay [EMD Millipore] will be conducted at the endpoint, following the manufacturer's instructions. Other additional biomarkers, assays, or methods can be included, but would not be crucial for this proposal. Comparison of activity among groups will be statistically analyzed by ANOVA.

Example 2

Conduct Pilot Study on its Applications in Vascularized Bone Tissue Engineering

Vascularization studies will be divided into two groups: (1) Treatment Group, and (2) Control Group. The bone scaffold will be synthesized as a composite of nanostructured calcium phosphate cement, and scaffold size determined based on a pilot study on cell density. A co-culture of bone marrow derived MSCs and peripheral blood derived EPCs with mixed media (bone media with endothelial supplements or endothelial-based media with osteoinductive supplements) will be seeded following protocols, as an alternative to the many different vascularization procedures in bone tissue scaffolds. Experiments will be conducted under four steady and pulsatile flow rates (at 0.05 Hz). Flow rate will be determined to yield an approximate FSS of 0.01, 0.05, 1, and 10 dyne/cm$^2$, for static, sub-threshold, and physiological mechanotransductive conditions. Scaffolds will be harvested at 1, 2, and 6 days; and cellular MTT activity assay will be performed, in addition to histology for measuring core density by cell type. The 3D velocity field profiles in each bioreactor condition will be monitored using holographic correlation velocimetry and then analyzed.

Example 3

Pre-diabetic T2D model using male obese prone rats vs lean rats (age-matched, fed ad libitum and fed-controlled groups) will be compared using 3D molecular imaging (IVIS) following intravenous injection of nanoparticle probes (NIR dyes) to monitor microcirculatory status over time of interest. Rats will be sacrificed at time points. Tissue will be isolated and homogenized for analysis, and histology of local sites of interest will be obtained, in control vs treated rats (treatment may be through functionalized nanoparticle probes, or other pharmaceutical/non-pharmaceutical intervention). Using these test systems, microcirculatory pathophysiology in the stomach preceding pancreatic damage, in addition to related speculative patterns on connective tissue (adipose) inflammation, are predicted in the model of interest. Providing data on the investigation of potential early associations among various connective tissue—organ systems or local (region-dependent) characterization in various chronic pathophysiologies will be gathered. At that time early-stage therapeutic strategies for patients can be developed [including, but not limited to, local delivery or manipulative methods (e.g. needle-based local guidance signaling or delivery with 'smart' carriers) and integrative practices (e.g. non-traumatic region-specific pulsatile blunt force targeting, transcutaneous electrical nerve stimulation, mind and body manipulation, photo/thermal/magnetic therapies), in addition to addressing safety, repeatability, and reproducibility concerns.

What is claimed is:

1. A nanoparticle probe comprising:
   a nanoparticle base structure coated with a biodegradable layer; and
   a slip bond moiety comprising a binding motif for a glycocalyx and having a binding strength to the glycocalyx of less than about 100 pN, wherein the slip bond moiety is configured to reversibly bind to the glycocalyx of a cell;
   a polymeric tether functionalized to the nanoparticle base structure and to an associative moiety comprising a cell surface binding moiety configured to bind to a one or more of a cell surface protein, receptor, and/or biomarker of the cell with a binding strength of larger than 100 pN;
   wherein the associative moiety preferentially binds to the protein, receptor, and/or biomarker of the cell based on the thickness of a glycocalyx layer of the cell.

2. The nanoparticle probe of claim 1, wherein the associative moiety comprises a ligand for a cell surface receptor and wherein the ligand binds to the cell surface receptor with a binding strength of greater than 500 pN.

3. The nanoparticle probe of claim 1, wherein the associative moiety comprises an oligonucleotide.

4. The nanoparticle probe of claim 1, wherein the slip bond moiety comprises one or more of a hyaluronan targeting motif, chondroitin sulfate targeting motif, dermatan sulfate targeting motif, heparan sulfate targeting motif, and/or combinations of the foregoing.

5. The nanoparticle probe of claim 1, wherein the nanoparticle base structure comprises a poly(amidoamine) (PAMAM) dendrimers, dendrimeric poly(l-lysine), dendrimeric polypropylenimine (PPI), Denkewalter-type PLL dendrimer, Tomalia-type PAMAM dendrimer, hydroxylated PAMAM dendrimer, Hult-type poly(ester) (bis-MPA) dendrimer, Majoral/Caminadetype phosphorous-based dendrimer, Simanek-type triazine based dendrimer, Jayaraman/Jain-type poly(propyletherimine) (PETIM) dendrimer, peptide dendrimer conjugate, or combinations thereof.

6. A method of diagnosing dysfunctional tissue in a patient comprising:
   administering the nanoparticle probe of claim 1 to the patient; and
   detecting the nanoparticle probe in the patient.

7. The nanoparticle probe of claim 1, wherein the biodegradable layer comprises one or more of poly-D-L-lactide-co-glycolide, polylactic acid, poly-ε-caprolactone, chitosan, gelatin, and poly-alkylcyanoacrylates.

8. The nanoparticle probe of claim 1, wherein the biodegradable layer encapsulates the tether.

9. The nanoparticle probe of claim 7, wherein the biodegradable layer is configured to thin over time to expose additional length of the tether.

10. The nanoparticle probe of claim 1, wherein the associative moiety comprises sialyl Lewis X.

11. The nanoparticle probe of claim 1, wherein the associative moiety comprises one or more of RGD, scFv, or sdAb.

12. The nanoparticle probe of claim 1, wherein the slip bond moiety comprises a lectin.

13. The nanoparticle probe of claim 1, wherein the slip bond moiety comprises an antibody.

14. The nanoparticle probe of claim 1, wherein the nanoparticle base structure comprises DNA origami or RNA origami.

15. The nanoparticle probe of claim 1, wherein the nanoparticle base structure comprises a gold nanoparticle, an iron-oxide nanoparticle, colloidal gold, TNF-bound colloidal gold, or combinations thereof.

16. The nanoparticle probe of claim 1, wherein the nanoparticle base structure comprises albumin, polystyrene latex particles, PEG-PLL, PEG-PAMAM, PETIM-DG, PEG-PPI, or combinations thereof.

* * * * *